(12) United States Patent
Folta

(10) Patent No.: US 10,801,023 B2
(45) Date of Patent: Oct. 13, 2020

(54) METHODS OF IDENTIFYING BIOLOGICALLY ACTIVE RANDOM PEPTIDES IN PLANTS AND LIBRARIES OF PLANTS EXPRESSING CANDIDATE BIOLOGICALLY ACTIVE RANDOM PEPTIDES

(71) Applicant: University of Florida Research Foundation, Inc., Gainesville, FL (US)

(72) Inventor: Kevin Michael Folta, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 83 days.

(21) Appl. No.: 15/790,639

(22) Filed: Oct. 23, 2017

(65) Prior Publication Data

US 2018/0051279 A1 Feb. 22, 2018

Related U.S. Application Data

(63) Continuation-in-part of application No. PCT/US2016/028797, filed on Apr. 22, 2016.

(60) Provisional application No. 62/152,189, filed on Apr. 24, 2015, provisional application No. 62/506,322, filed on May 15, 2017.

(51) Int. Cl.
| | | |
|---|---|---|
| *C12N 15/10* | (2006.01) | |
| *C07K 7/06* | (2006.01) | |
| *C12N 15/82* | (2006.01) | |
| *C07K 7/08* | (2006.01) | |

(52) U.S. Cl.
CPC ........... *C12N 15/1079* (2013.01); *C07K 7/06* (2013.01); *C07K 7/08* (2013.01); *C12N 15/827* (2013.01); *C12N 15/8209* (2013.01)

(58) Field of Classification Search
None
See application file for complete search history.

(56) References Cited

U.S. PATENT DOCUMENTS

2011/0162109 A1 6/2011 Himanen et al.

FOREIGN PATENT DOCUMENTS

| EP | 0723019 | * 10/1988 | ............. C12N 15/82 |
|---|---|---|---|
| GB | 2130219 | 5/1984 | |
| WO | 0005406 | 2/2000 | |

OTHER PUBLICATIONS

JP 152896, Genbank, TSA: Ipomoea batatas Contig_ 48308.Ipbalsr mRNA sequence- Nucleotide- NCBI, 1 page.

International Search Report, dated Oct. 24, 2016, for application No. PCT/US2016/28797, 47 pages.
Adessi C, Soto C (2002) Converting a peptide into a drug: strategies to improve stability and bioavailability. Current medicinal chemistry 9: 963-978.
Blümel M, Daily N, Jung C (2015) Flowering time regulation in crops —what did we learn from *Arabidopsis*? Current Opinion in Biotechnology 32: 121-129.
Breiden M, Simon R (2016) Q&A: How does peptide signaling direct plant development? BMC Biology 14: 58.
Cardó-Vila M, Giordano RJ, Sidman RL, Bronk LF, Fan Z, Mendelsohn J, Arap W, Pasqualini R (2010) From combinatorial peptide selection to drug prototype (II): Targeting the epidermal growth factor receptor pathway. Proceedings of the National Academy of Sciences 107: 5118-5123.
Clough SJ, Bent AF (1998) Floral dip: a simplified method for Agrobacterium-mediated transformation of *Arabidopsis thaliana*. Plant J 16: 735-743.
Duke SO, Lydon J, Jos, xe, Becerril M, Sherman TD, Lehnen LP, Matsumoto H (1991) Protoporphyrinogen Oxidase-Inhibiting Herbicides. Weed Science 39: 465-473.
Edwards K, Johnstone C, Thompson C (1991) A simple and rapid method for the preparation of plant genomic DNA for PCR analysis. Nucleic Acids Res 19: 1349.
Gaspar T, Kevers C, Debergh P, Maene L, Paques M, Boxus P (1987) Vitrification: Morphological, Physiological, and Ecological Aspects. In JM Bonga, DJ Durzan, eds, Cell and Tissue Culture in Forestry: General Principles and Biotechnology. Springer Netherlands, Dordrecht, pp. 152-166.
Hamzeh-Mivehroud M, Alizadeh AA, Morris MB, Bret Church W, Dastmalchi S (2013) Phage display as a technology delivering on the promise of peptide drug discovery. Drug Discovery Today 18: 1144-1157.
Higashijima T, Uzu S, Nakajima T, Ross EM (1988) Mastoparan, a peptide toxin from wasp venom, mimics receptors by activating GTP-binding regulatory proteins (G proteins). Journal of Biological Chemistry 263: 6491-6494.
Jorgensen RA, Cluster PD, English J, Que Q, Napoli CA (1996) Chalcone synthase cosuppression phenotypes in petunia flowers: comparison of sense vs. antisense constructs and single-copy vs. complex T-DNA sequences. Plant molecular biology 31: 957-973.
Karimi M, Inze D, Depicker A (2002) Gateway vectors for Agrobacterium-mediated plant transformation. Trends Plant Sci 7: 193-195.
Keller MM, Jaillais Y, Pedmale UV, Moreno JE, Chory J, BallaréCL (2011) Cryptochrome 1 and phytochrome B control shade-avoidance responses in *Arabidopsis* via partially independent hormonal cascades. The Plant Journal 67: 195-207.
Kevers C, Franck T, Strasser RJ, Dommes J, Gaspar T (2004) Hyperhydricity of Micropropagated Shoots: A Typically Stress-induced Change of Physiological State. Plant Cell, Tissue and Organ Culture 77: 181-191.

(Continued)

*Primary Examiner* — Robert H Havlin
(74) *Attorney, Agent, or Firm* — Thomas | Horstemeyer, LLP

(57) ABSTRACT

The present disclosure provides methods and systems for identifying biologically active random peptides (BARPs) in plants. The present disclosure also provides libraries of transformed plants, where each plant expresses a different candidate BARP. Also provided are engineered, isolated BARPs capable of producing a non-wild type phenotype in plants.

12 Claims, 15 Drawing Sheets

Specification includes a Sequence Listing.

(56) References Cited

OTHER PUBLICATIONS

Ladner RC, Sato AK, Gorzelany J, de Souza M (2004) Phage display-derived peptides as therapeutic alternatives to antibodies. Drug Discovery Today 9: 525-529.

Lindell TJ, Weinberg F, Morris PW, Roeder RG, Rutter WJ (1970) Specific inhibition of nuclear RNA polymerase II by alpha-amanitin. Science 170: 447-449.

Mitter N, Worrall EA, Robinson KE, Li P, Jain RG, Taochy C, Fletcher SJ, Carroll BJ, Lu GQM, Xu ZP (2017) Clay nanosheets for topical delivery of RNAi for sustained protection against plant viruses. Nature Plants 3: 16207.

Moreland DE (1980) Mechanisms of action of herbicides. Annual Review of plant physiology 31: 597-638.

Neff MM, Chory J (1998) Genetic interactions between phytochrome A, phytochrome B, and cryptochrome 1 during *Arabidopsis* development. Plant Physiol 118: 27-35.

Nixon AE, Sexton DJ, Ladner RC (2014) Drugs derived from phage display: From candidate identification to clinical practice. mAbs 6: 73-85.

Parks BM, Folta KM, Spalding EP (2001) Photocontrol of stem growth. Curr Opin Plant Biol 4: 436-440.

Ramachandran KV, Margolis SS (2017) A mammalian nervous-system-specific plasma membrane proteasome complex that modulates neuronal function. Nat Struct Mol Biol 24: 419-430.

Smith GP, Petrenko VA (1997) Phage Display. Chemical Reviews 97: 391-410.

Valverde F, Mouradov A, Soppe W, Ravenscroft D, Samach A, Coupland G (2004) Photoreceptor regulation of CONSTANS protein in photoperiodic flowering. Science 303: 1003-1006.

\* cited by examiner

SEQ ID NO: 1

AAAAGCAGGCTCCATGGCCTGTNNNNNNNNNNNNNNNNNNTGTTAGACCC

Vector Seq    Start Ala Cys    ---18 random nt---    Cys Stop Gateway
                                                 (6 random codons)

FIG. 1

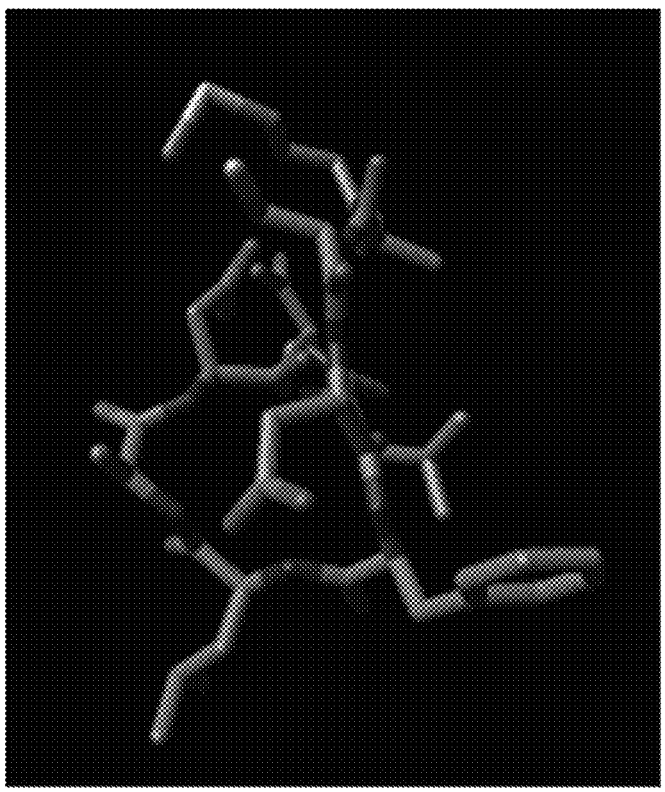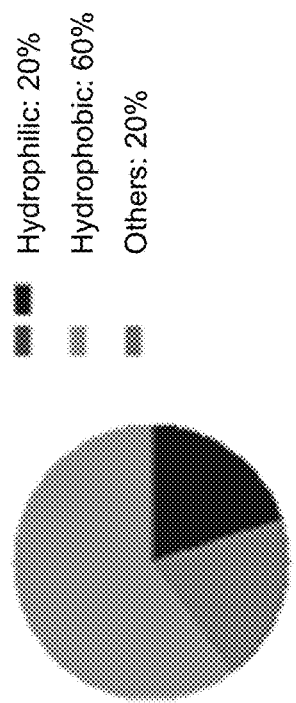
FIG. 3B
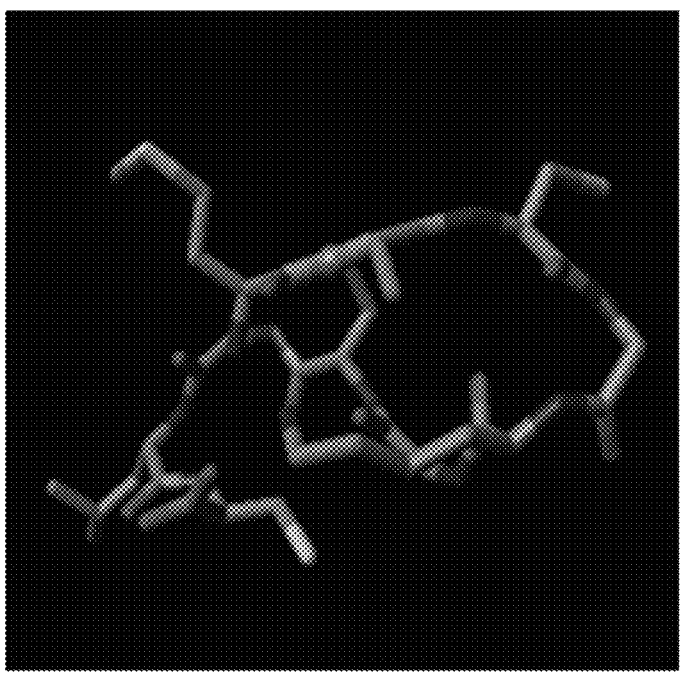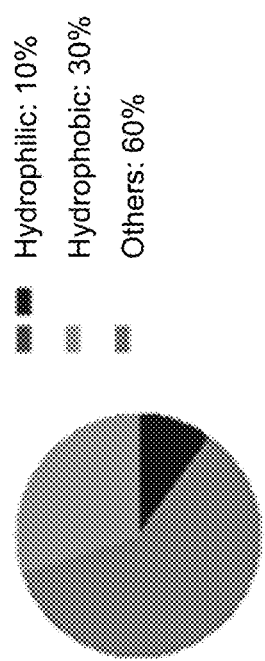
FIG. 3A

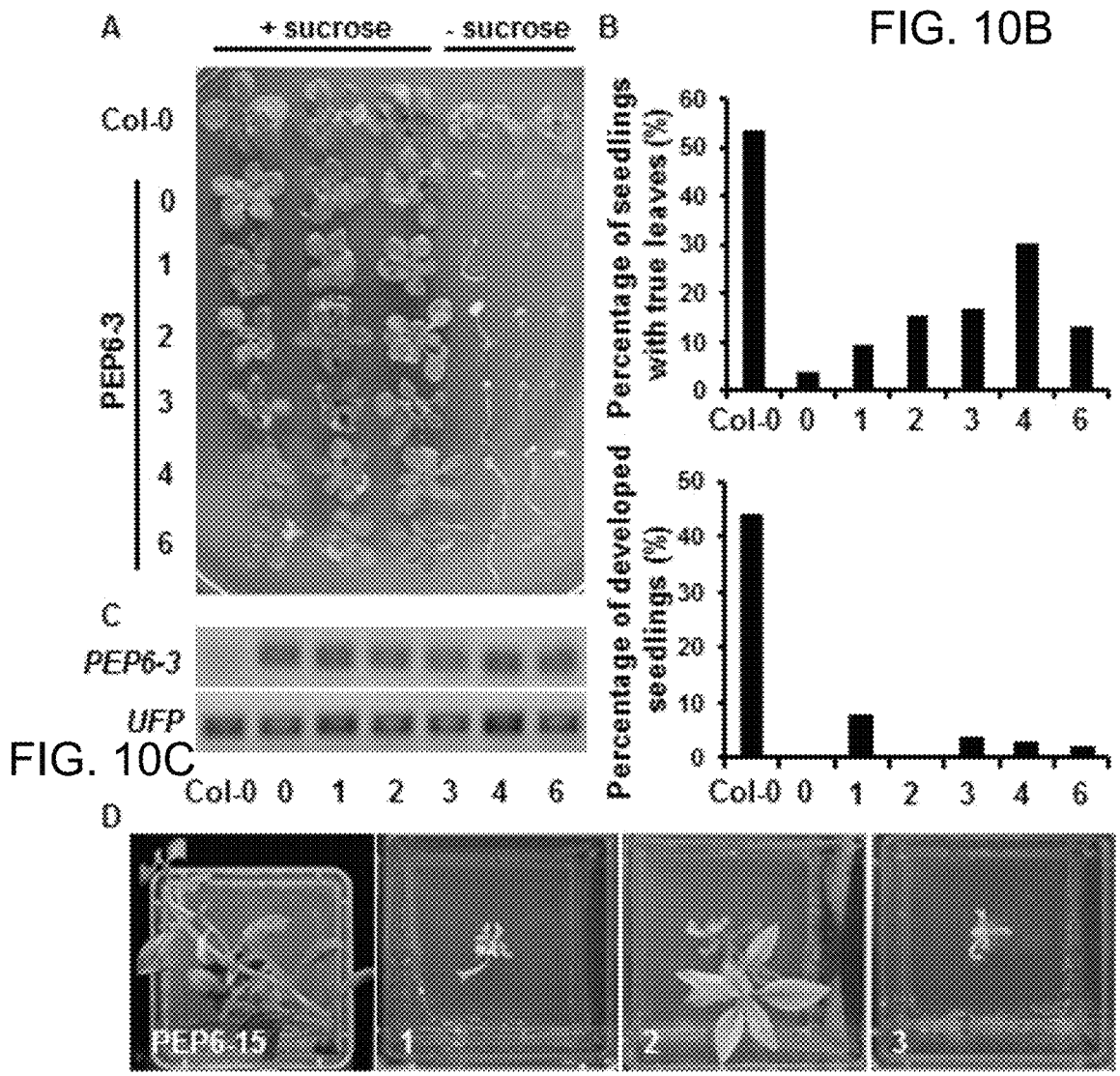

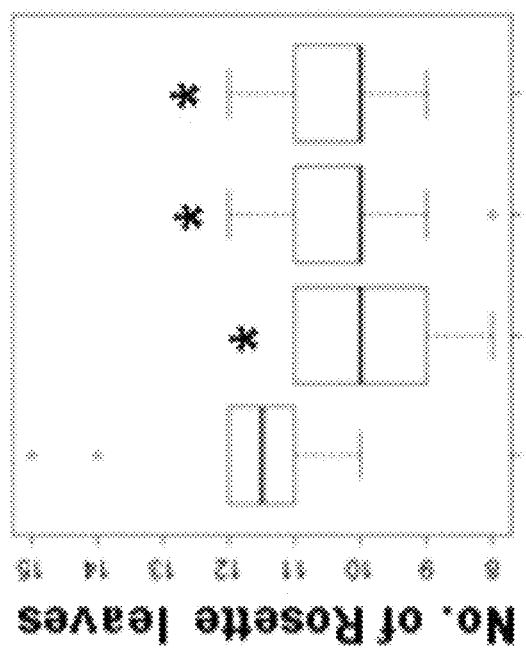
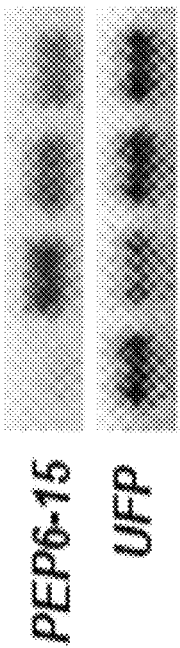
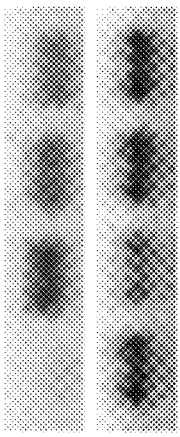
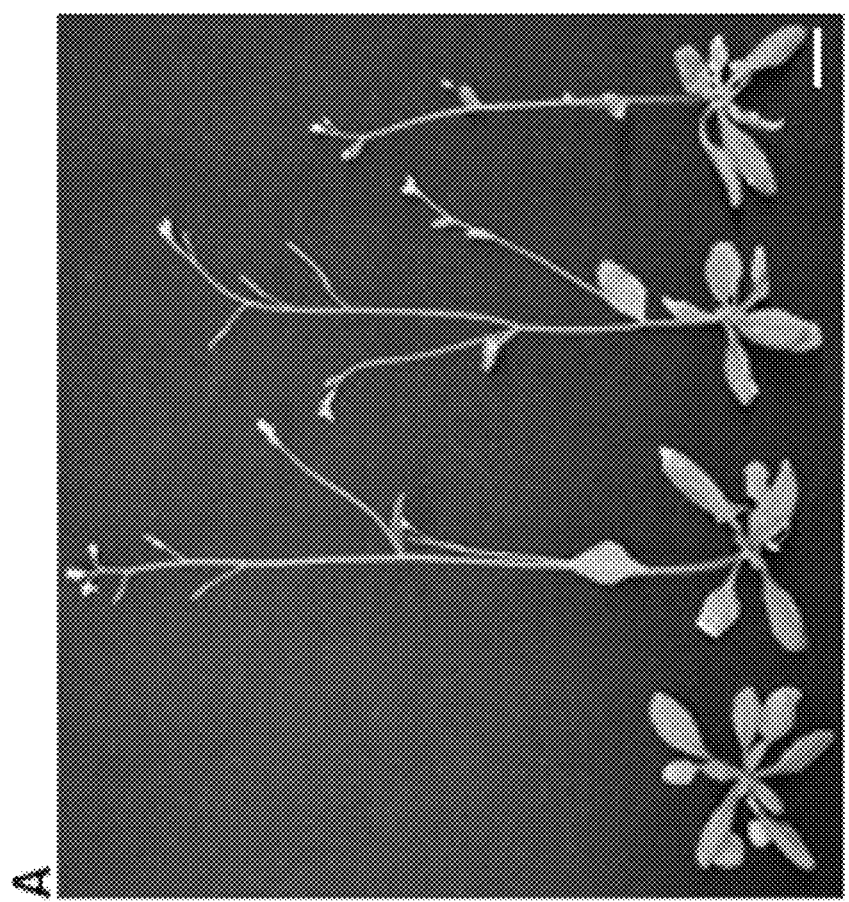
FIG. 11A
FIG. 11B
FIG. 11C

FIG. 13A
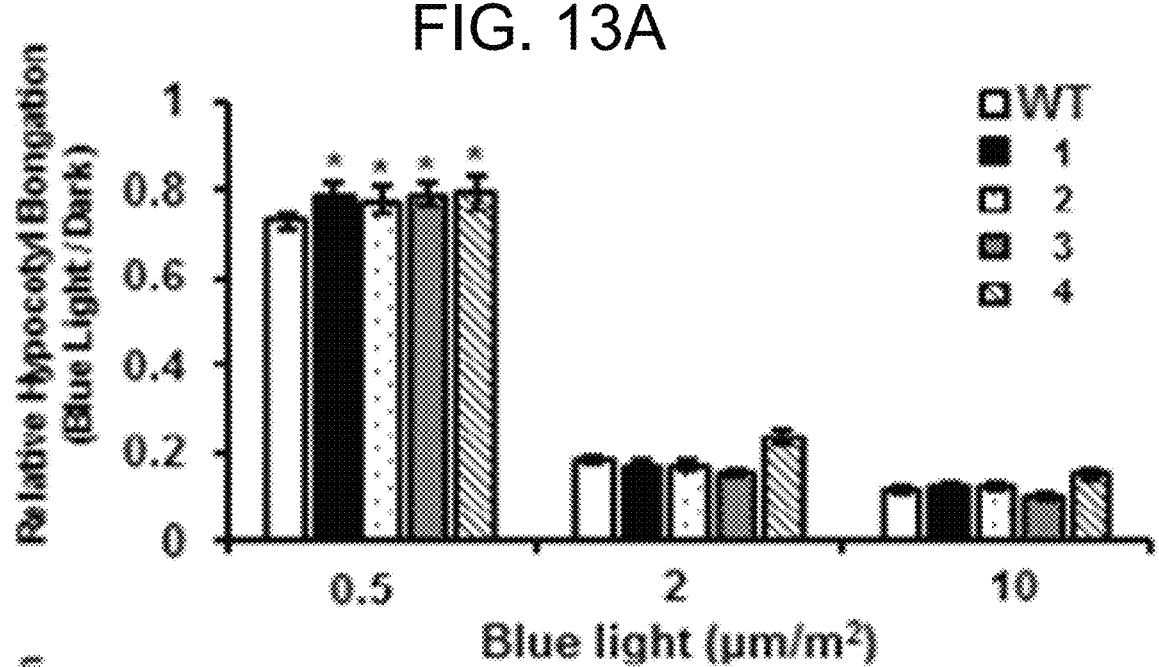
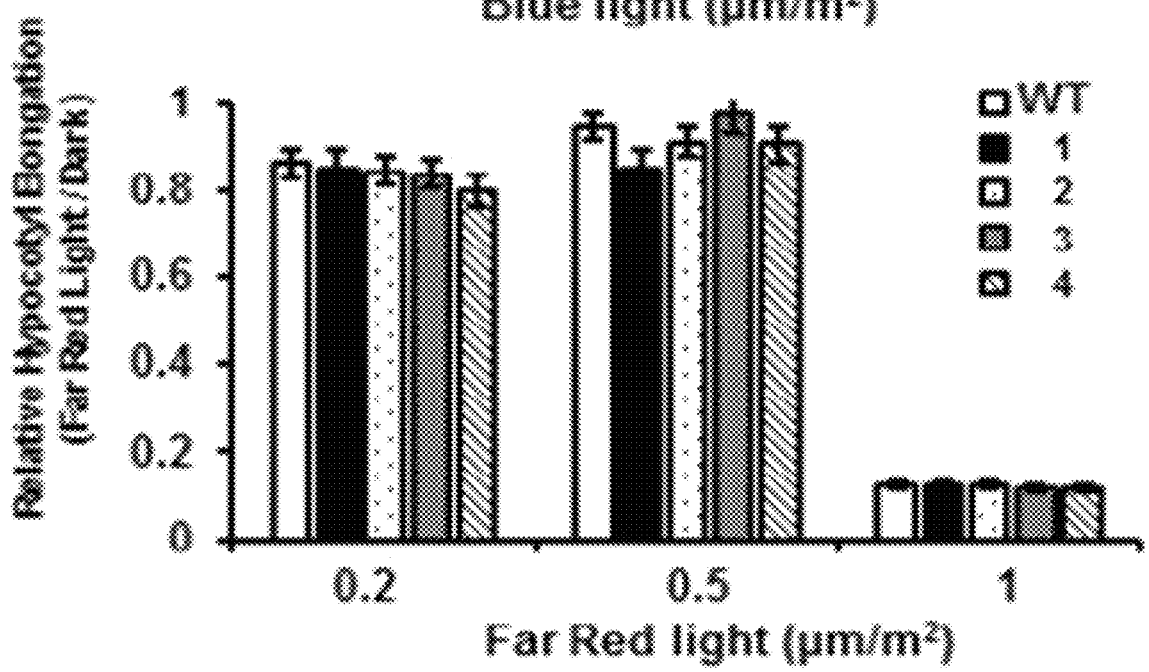
FIG. 13B

SEQUENCE LISTING

<160> NUMBER OF SEQ ID NOS: 38

<210> SEQ ID NO 1
<211> LENGTH: 50
<212> TYPE: DNA
<213> ORGANISM: Artificial Sequence
<220> FEATURE:
<223> OTHER INFORMATION: chemically synthesized nucleic acid sequence
      including a test nucleic acid sequence encoding a random peptide
      sequence for a candidate biologically active random peptide having
      6 random amino acids
<220> FEATURE:
<221> NAME/KEY: misc_feature
<222> LOCATION: (23)..(60)
<223> OTHER INFORMATION: n is any nucleotide

<400> SEQUENCE: 1
aaaaggaggc tccatggcct gtnnnnnnnn nnnnnnnnnn tgttagaccc 50

<210> SEQ ID NO 2
<211> LENGTH: 10
<212> TYPE: PRT
<213> ORGANISM: Artificial Sequence
<220> FEATURE:
<223> OTHER INFORMATION: chemically synthesized peptide sequence of BARP associated with purple pigment accumulation in seed pods

<400> SEQUENCE: 2

Met Ala Cys Gly Lys Gly Ser Gly Leu Cys
1 5 10

<210> SEQ ID NO 3
<211> LENGTH: 10
<212> TYPE: PRT
<213> ORGANISM: Artificial Sequence
<220> FEATURE:
<223> OTHER INFORMATION: chemically synthesized peptide sequence of BARP associated with bushy seedling phenotype

<400> SEQUENCE: 3

Met Ala Cys Asp Phe Leu Ala Asp Leu Cys
1 5 10

<210> SEQ ID NO 4
<211> LENGTH: 10
<212> TYPE: PRT
<213> ORGANISM: Artificial Sequence
<220> FEATURE:
<223> OTHER INFORMATION: chemically synthesized peptide sequence of BARP associated with abberrant seedling characteristics

<400> SEQUENCE: 4

Met Ala Cys Ser Ala His Cys Ser Asp Cys
1 5 10

<210> SEQ ID NO 5
<211> LENGTH: 33
<212> TYPE: DNA
<213> ORGANISM: Artificial Sequence
<220> FEATURE:
<223> OTHER INFORMATION: chemically synthesized test nucleotide sequence encoding a BARP having 6 random amino acids
<220> FEATURE:
<221> NAME/KEY: misc_feature
<222> LOCATION: (10)..(27)
<223> OTHER INFORMATION: n is any nucleotide

<400> SEQUENCE: 5
atggcctgtn nnnnnnnnnn nnnnnnntgt tag 33

<210> SEQ ID NO 6
<211> LENGTH: 10
<212> TYPE: PRT
<213> ORGANISM: Artificial Sequence
<220> FEATURE:
<223> OTHER INFORMATION: chemically synthesized peptide sequence of BARP CBF6AA-15 associated with early flowering behavior

<400> SEQUENCE: 6

Met Ala Cys Asp Phe Asn Phe Gly Ile Cys
1 5 10

<210> SEQ ID NO 7
<211> LENGTH: 6
<212> TYPE: PRT

```
<213> ORGANISM: Artificial Sequence
<220> FEATURE:
<223> OTHER INFORMATION: chemically synthesized peptide sequence of BARP
      CBF6AA-85 associated with large, flat leaves and small petioles

<400> SEQUENCE: 7

Met Ala Cys Lys Gln Ala
1               5

<210> SEQ ID NO 8
<211> LENGTH: 10
<212> TYPE: PRT
<213> ORGANISM: Artificial Sequence
<220> FEATURE:
<223> OTHER INFORMATION: chemically synthesized peptide sequence of BARP
      CBF6AA-110 associated with large, flat leaves and small petioles

<400> SEQUENCE: 8

Met Ala Cys Trp Thr Ser Ser Val Leu Cys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: chemically synthesized peptide sequence of BARP
      12AA-97 associated with arrested plant growth

<400> SEQUENCE: 9

Met Gly Cys Val Cys Ile Glu Pro Tyr Gln Arg Leu Arg Ala Lys Cys
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: chemically synthesized peptide sequence of BARP
      6AA-33.1 associated with salt resistance and elongated root growth

<400> SEQUENCE: 10

Met Ala Cys Pro Ala Ser Val Ser Val Cys
1               5                   10

<210> SEQ ID NO 11
<211> LENGTH: 59
<212> TYPE: DNA
<213> ORGANISM: Artificial Sequence
<220> FEATURE:
<223> OTHER INFORMATION: chemically synthesized nucleic acid sequence
      including a test nucleic acid sequence encoding a random peptide
      sequence for a candidate biologically active random peptide having
      6 random amino acids
<220> FEATURE:
<221> NAME/KEY: misc_feature
<222> LOCATION: (24)..(41)
<223> OTHER INFORMATION: n is any nucleotide

<400> SEQUENCE: 11
aaaaaggagg ctccatggcc tgtnnnnnnn nnnnnnnnnn ntgttagacc cagctttct      59

<210> SEQ ID NO 12
<211> LENGTH: 78
<212> TYPE: DNA
<213> ORGANISM: Artificial Sequence
<220> FEATURE:
<223> OTHER INFORMATION: chemically synthesized nucleic acid sequence
      including a test nucleic acid sequence encoding a random peptide
``` sequence for a candidate biologically active random peptide having
12 random amino acids
<220> FEATURE:
<221> NAME/KEY: misc_feature
<222> LOCATION: (25)..(60)
<223> OTHER INFORMATION: n is any nucleotide

<400> SEQUENCE: 12
aaaaaggagg ctccatgggc ctgtnnnnnn nnnnnnnnnn nnnnnnnnnn nnnnnnnnnn    60
tgttagaccc agctttct                                                 78

<210> SEQ ID NO 13
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-3

<400> SEQUENCE: 13
atggcctgtc gtggtgttga tagtgcttgt tag                                33

<210> SEQ ID NO 14
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-3

<400> SEQUENCE: 14

Met Ala Cys Arg Gly Val Asp Ser Ala Cys
1               5                   10

<210> SEQ ID NO 15
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-12

<400> SEQUENCE: 15
atggcctgtt ggatgtcgag gatggagtgt tag                                33

<210> SEQ ID NO 16
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-12

<400> SEQUENCE: 16

Met Ala Cys Trp Met Ser Arg Met Glu Cys
1               5                   10

<210> SEQ ID NO 17
<211> LENGTH: 32
<212> TYPE: DNA
<213> ORGANISM: Artificial Sequence
<220> FEATURE:
<223> OTHER INFORMATION: chemically synthesized nucleotide sequence
      encoding BARP PEP6-15

<400> SEQUENCE: 17
atggcctgtg atttaatttt ggtatttgtt ag                                 32

<210> SEQ ID NO 18
<211> LENGTH: 33
<212> TYPE: DNA
<213> ORGANISM: Artificial Sequence
<220> FEATURE:
<223> OTHER INFORMATION: chemically synthesized nucleotide encoding BARP
      PEP6-27

<400> SEQUENCE: 18
atggcctgta attgttcttc tgatggttgt tag                                33

<210> SEQ ID NO 19
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-27

<400> SEQUENCE: 19

Met Ala Cys Asn Cys Ser Ser Asp Gly Cys
1               5                   10

<210> SEQ ID NO 20
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-28

<400> SEQUENCE: 20
atggcctgtc agctgatgtg gcgggagtgt tag                                33

<210> SEQ ID NO 21
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-28

<400> SEQUENCE: 21

Met Ala Cys Gln Leu Met Trp Arg Glu Cys
1               5                   10

<210> SEQ ID NO 22
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-30

<400> SEQUENCE: 22
atggcctgtc aggagctgac gatgtggtgt tag                                33

<210> SEQ ID NO 23
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-30

<400> SEQUENCE: 23

```
Met Ala Cys Gln Glu Leu Thr Met Trp Cys
1               5                   10
```

<210> SEQ ID NO 24
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-32

<400> SEQUENCE: 24
atggcctgtc ctgcttctgt tagtgtttgt tag                33

<210> SEQ ID NO 25
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-33

<400> SEQUENCE: 25
atggcctgtc ctaatgcttg tttttcttgt tag                33

<210> SEQ ID NO 26
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-33

<400> SEQUENCE: 26

```
Met Ala Cys Pro Asn Ala Cys Phe Ser Cys
1               5                   10
```

<210> SEQ ID NO 27
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-37

<400> SEQUENCE: 27
atggcctgtc agcagatgtt gtcggggtgt tag                33

<210> SEQ ID NO 28
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-37

<400> SEQUENCE: 28

```
Met Ala Cys Gln Gln Met Leu Ser Gly Cys
1               5                   10
```

<210> SEQ ID NO 29
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-38

<400> SEQUENCE: 29
atggcctgtt ctgatgttag tgttatttgt tag          33

<210> SEQ ID NO 30
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-38

<400> SEQUENCE: 30

Met Ala Cys Ser Asp Val Ser Val Ile Cys
1               5                   10

<210> SEQ ID NO 31
<211> LENGTH: 33
<212> TYPE: DNA
<213> ORGANISM: Artificial Sequence
<220> FEATURE:
<223> OTHER INFORMATION: chemically synthesized nucleotide sequence
      encoding BARP PEP6-46

<400> SEQUENCE: 31
atggcctgtg gtggtggttg ttctgcttgt tag          33

<210> SEQ ID NO 32
<211> LENGTH: 10
<212> TYPE: PRT
<213> ORGANISM: Artificial Sequence
<220> FEATURE:
<223> OTHER INFORMATION: chemically synthesized peptide sequence of BARP
      PEP6-46

<400> SEQUENCE: 32

Met Ala Cys Gly Gly Gly Cys Ser Ala Cys
1               5                   10

<210> SEQ ID NO 33
<211> LENGTH: 29
<212> TYPE: DNA
<213> ORGANISM: Artificial Sequence
<220> FEATURE:
<223> OTHER INFORMATION: chemically synthesized primer attB1 adaptor
      primer

<400> SEQUENCE: 33
ggggacaagt ttgtacaaaa aagcaggct              29

<210> SEQ ID NO 34
<211> LENGTH: 29
<212> TYPE: DNA
<213> ORGANISM: Artificial Sequence
<220> FEATURE:
<223> OTHER INFORMATION: chemically synthesized primer attB2 adaptor
      primer

<400> SEQUENCE: 34
ggggaccact ttgtacaaga aagctgggt              29

<210> SEQ ID NO 35
<211> LENGTH: 22
<212> TYPE: DNA
<213> ORGANISM: Artificial Sequence
<220> FEATURE:
<223> OTHER INFORMATION: chemically synthesized primer PEP-F

```
<400> SEQUENCE: 35
cgtaagggat gacgcacaat cc                                              22

<210> SEQ ID NO 36
<211> LENGTH: 22
<212> TYPE: DNA
<213> ORGANISM: Artificial Sequence
<220> FEATURE:
<223> OTHER INFORMATION: chemically synthesized primer PEP-R

<400> SEQUENCE: 36
gagcgaaacc ctataagaac cc                                              22

<210> SEQ ID NO 37
<211> LENGTH: 24
<212> TYPE: DNA
<213> ORGANISM: Artificial Sequence
<220> FEATURE:
<223> OTHER INFORMATION: chemically synthesized primer PEP-rF

<400> SEQUENCE: 37
ccagcagaca tggaggtttt gggg                                            24

<210> SEQ ID NO 38
<211> LENGTH: 25
<212> TYPE: DNA
<213> ORGANISM: Artificial Sequence
<220> FEATURE:
<223> OTHER INFORMATION: chemically synthesized primer PEP-rR

<400> SEQUENCE: 38
tgttgtctgt catttcttgg ccagt                                           25
```

METHODS OF IDENTIFYING BIOLOGICALLY ACTIVE RANDOM PEPTIDES IN PLANTS AND LIBRARIES OF PLANTS EXPRESSING CANDIDATE BIOLOGICALLY ACTIVE RANDOM PEPTIDES

CROSS-REFERENCE TO RELATED APPLICATIONS

This application is a continuation-in-part of PCT Application No. PCT/US2016/028797, filed Apr. 22, 2016 and entitled "METHODS OF IDENTIFYING BIOLOGICALLY ACTIVE RANDOM PEPTIDES IN PLANTS AND LIBRARIES OF PLANTS EXPRESSING CANDIDATE BIOLOGICALLY ACTIVE RANDOM PEPTIDES," where the PCT claimed priority to and the benefit of U.S. Provisional Patent Application No. 62/152,189, filed on Apr. 24, 2015, having the same title, both of which are incorporated by reference herein in their entireties. This application also claims the benefit of and priority to U.S. Provisional Patent Application No. 62/506,322, filed on May 15, 2017, entitled "METHODS OF IDENTIFYING BIOLOGICALLY ACTIVE RANDOM PEPTIDES IN PLANTS AND LIBRARIES OF PLANTS EXPRESSING CANDIDATE BIOLOGICALLY ACTIVE RANDOM PEPTIDES," the contents of which is incorporated by reference herein in its entirety.

SEQUENCE LISTING

This application contains a sequence listing filed in electronic form as an ASCII.txt file entitled 222109-1370_ST25.K created on Oct. 23, 2017 and having a size of 11 KB. The content of the sequence listing is incorporated herein in its entirety.

BACKGROUND

A tremendous need exists for new and environmentally friendly plant growth regulators, developmental modulators, and herbicides. Everything we eat, most of the clothes we wear, and the oxygen we breathe comes directly or indirectly from plants. Farmers worldwide battle old and new challenges and seek new technology to mitigate barriers to profitable production. From changing climates, emerging pathogens, new pests, phase-out of effective chemical controls, decreased fertilizer use, and high costs of labor and chemicals, farmers need new products to enhance plant production. At the same time, new technologies must be environmentally friendly, and pose minimal risk to humans and other animals that consume treated plant products Scientists use a process called chemical genomics to identify key regulatory molecules that influence specific biological processes. Chemical genomics involves the identification of novel applications for known compounds. The approach applies individual chemicals from 'libraries' of compounds to an animal, plant, bacterium or fungus, and then searches for changes. In plants and animals this approach is used to identify new potential drugs or growth regulators that are neither anticipated nor designed; instead, they are a chance consequence of chemical interaction that triggers a reproducible response. Chemical genomics screens a library of thousands of compounds to identify those that elicit a desired effect.

Using a technique such as chemical genomics to screen libraries of peptides for biological activity in plants involves manufacturing the peptides and treating plants with these peptides. This approach presents several challenges, such as, but not limited to, expensive peptide synthesis, achieving sufficient peptide uptake into the cells of the plant, time required for plant growth followed by peptide application and observation, and the ability to test only certain stages of plant development. Thus, the field needs alternative methods for screening libraries of compounds for biological activity in plants and identifying novel biologically-active compounds.

SUMMARY

The present disclosure provides methods for identifying biologically active random peptides (BARPs) in plants. In embodiments, such methods include providing a library of test nucleic acid sequences, as described above. The library includes a plurality of different test nucleic acid sequences encoding a plurality of candidate BARPs, where each test nucleic acid sequence includes nucleic acids encoding a start codon, a random sequence of amino acids representing a candidate BARP, and a stop codon. The methods further include creating a library of recombination vectors from the library of test nucleic acid sequences, where each vector includes a test nucleic acid sequence from the library and a nucleic acid sequence encoding a selectable marker operably linked to the test nucleic acid sequence. The method includes transforming a plurality of phenotypically homogenous plants of the same species with the library of recombination vectors. Then, the plants are screened for the presence of the selectable marker to select plants with the selectable marker to produce a library of transformed plants, where each plant includes a recombination vector from the library and identification of the selectable marker indicates expression of a candidate BARP by the plant. Finally the library of recombinant plants is screened throughout development for the occurrence of a plant with a new phenotype, where the new phenotype is discernible from the phenotype of a wild type plant and where the presence of the new phenotype indicates the candidate BARP in the plant with the new phenotype is responsible for the new phenotype. In embodiments, upon identification of a new phenotype, the method further includes determining the sequence of the candidate BARP from the plant with the new phenotype.

The present disclosure further provides libraries of transformed plants. In embodiments, libraries of transformed plants of the present disclosure include a plurality of plants of the same species, each plant including a different recombination vector. In embodiments, each recombination vector includes a test nucleic acid sequence and a nucleic acid sequence encoding a selectable marker operably linked to the test nucleic acid sequence. The test nucleic acid sequence encodes a candidate biologically active random peptide (BARP), where each test nucleic acid sequence includes nucleic acids encoding at least the following: a start codon, a random sequence of at least 6 amino acids representing the candidate BARP, and a stop codon, where the test nucleic acid sequence in each vector encodes a different random sequence of amino acids and where the plurality of plants is phenotypically homogeneous in the absence of the recombination vector.

In embodiments, the present disclosure also provides, engineered, isolated peptides representing isolated, biologically active random peptides (BARPs) that produce a new phenotype in a plant having the BARP. In embodiments, the present disclosure provides engineered, isolated peptides of the present disclosure having a sequence selected from: SEQ ID NOs: 2, 4, 6, 7, 8, 9, 10, 14, 16, 19, 21, 23, 26, 28, 30, and 32.

Embodiments of the present disclosure also include transgenic plants that produce a non-native biologically active random peptide (BARP) of the present disclosure, such as, but not limited to, a BARP having a sequence selected from: SEQ ID NOs: 2, 4, 6, 7, 8, 9, 10, 14, 16, 19, 21, 23, 26, 28, 30, and 32.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1 illustrates an embodiment of a degenerative DNA oligonucleotide sequence (SEQ ID NO: 1, where N can be A, G, C, or T, such that each group of three N's "NNN" encodes an amino acid) used to generate a library of different sequences for use in a recombination-cloning system that then can be individually installed into plants, each capable of making a discrete peptide.

FIG. 2A shows an example of a probable herbicidal peptide, with the plant in the center exhibiting a phenotype of reduced growth and development, followed by death. FIG. 2B shows one plant that flowered early and produced seeds (yellow arrow) when all others remained vegetative, illustrating an early flowering phenotype induced by a candidate BARP. FIG. 2C illustrates an *Arabidopsis* plant with a phenotype exhibiting reduced size and aberrant leaf production, which can be compared against normal plant phenotypes in FIGS. 2A and 2B.

FIGS. 3A-3C illustrate 3-D models (top) and amino acid characteristics (bottom pie charts) of embodiments of three peptides that exhibited biological effects with an observable phenotype. In FIG. 3A, the sequence MACGKGSGLC (SEQ ID NO: 2) causes plants to hyper-accumulate purple pigments in the seed pods. The sequence, MACDFLADLC (SEQ ID NO: 3), illustrated in FIG. 3B results in a "bushy" seedling that produces small and upright leaves. The sequence illustrated in FIG. 3C, MACSAHCSDC (SEQ ID NO: 4), was isolated from plants exhibiting strange seedling characteristics. This figure shows that diverse peptide sequences with different characteristics can be isolated from plants with unusual phenotypes.

FIG. 4A is a digital image comparing a wild type *A. thaliana* plant with 3 separate lines transformed with the 6AA-15 BARP. A bar graph comparing the number of rosette leaves for each line at the time of flowering is illustrated in FIG. 4B.

FIG. 7A is a bar graph illustrating root growth of wild type plants vs. transformed plants through day 8 of growth. FIG. 7B is a digital image of wild type (right) and BARP transformed plants (left) grown on vertical agar plates showing the difference in root growth.

FIGS. 10A-10D illustrate *Arabidopsis* transgenic plants with rpORF PEP6-3 exhibit arrested growth phenotype at the seedling stage. FIG. 10A: Morphology of three-week old seedlings grown on ½ MS plates with and without sucrose. PEP6-3 and rpORF transgenic control lines were grown with sucrose did not show significant morphological differences. Without sucrose, control plants developed into mature seedlings whereas transgenic plants grew slowly with pale green leaves and ceased development. FIG. 10B: Percentage of seedlings with two true leaves and developed seedlings. FIG. 10C: Semi-quantitative RT-PCR analysis of rpORF PEP6-3 transcript accumulation. Each RT-PCR was for 25 cycles to detect the PEP6-3 transcript or the control gene Ubiquitin family protein (UFP, At4g01000). Transgenic line 0 is isolated from the original screening, and other five lines 1, 2, 3, 4 and 6 are isolated as independent transgenic lines from the retransformation. FIG. 10D: The same construct containing the rpORF PEP6-3 used in *Arabidopsis* transformation were introduced into Petunia. Another rpORF PEP6-15 was used as a control. Shown are transgenic seedlings grown on rooting media for more than one month.

FIGS. 11A-11C illustrate that overexpression of rpORF PEP6-15 resulted in earlier flowering phenotype. FIG. 11A: Morphology of four-week old seedlings. Three independent transgenic lines 1, 2 and 3 bolted earlier than Col-0. FIG. 11B: Comparison of flowering time in Col-0, transgenic lines 1, 2 and 3 grown under 16 hour light/8 hour dark condition (each genotype, n=30). Number of rosette leaves for each genotype was present in a box plot using R. The asterisk indicates a statistically significant difference from Col-0 as determined by Mann-Whitney U test. FIG. 11C:

RT-PCR analysis of rpORF PEP6-15 transcription. Each RT-PCR was for 25 cycles to detect the transcription of PEP6-15 or UFP.

Figure 12B:
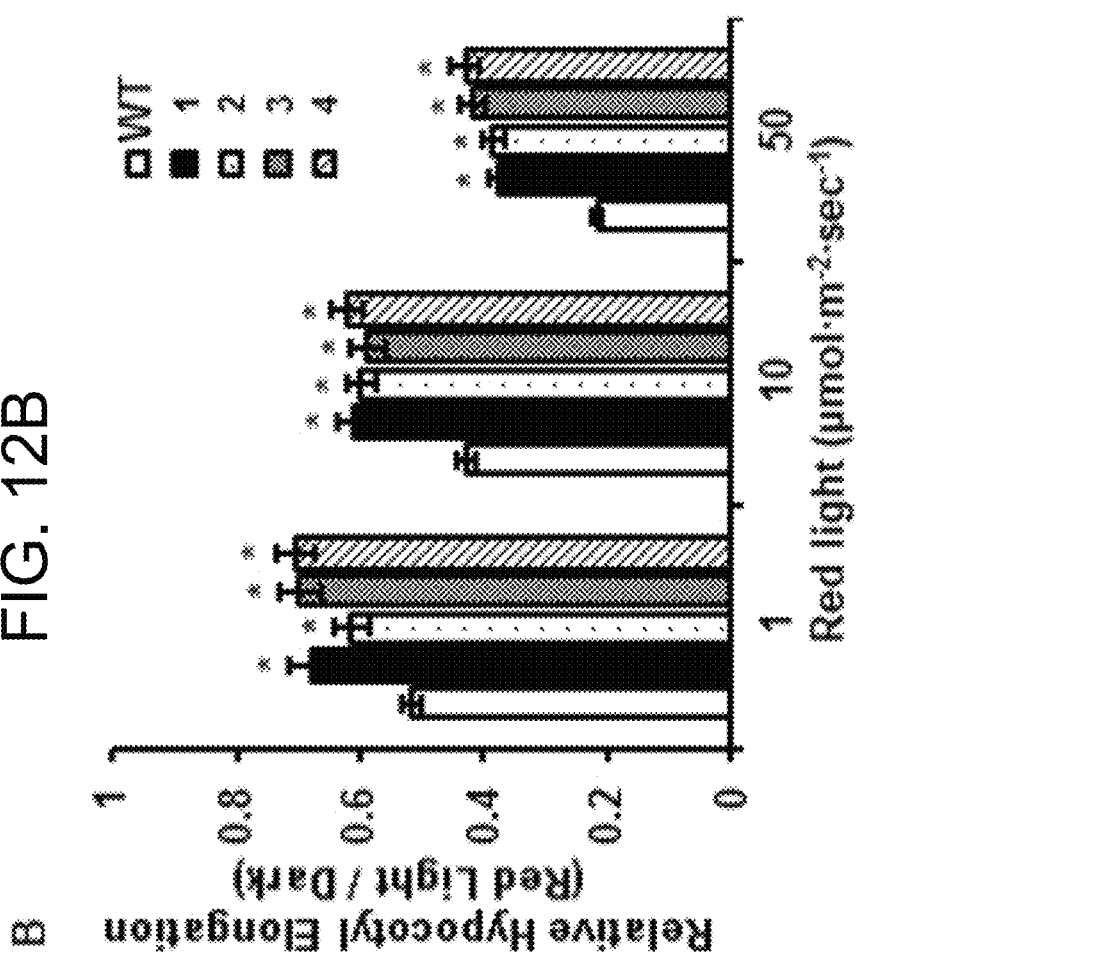
Figure 12A:
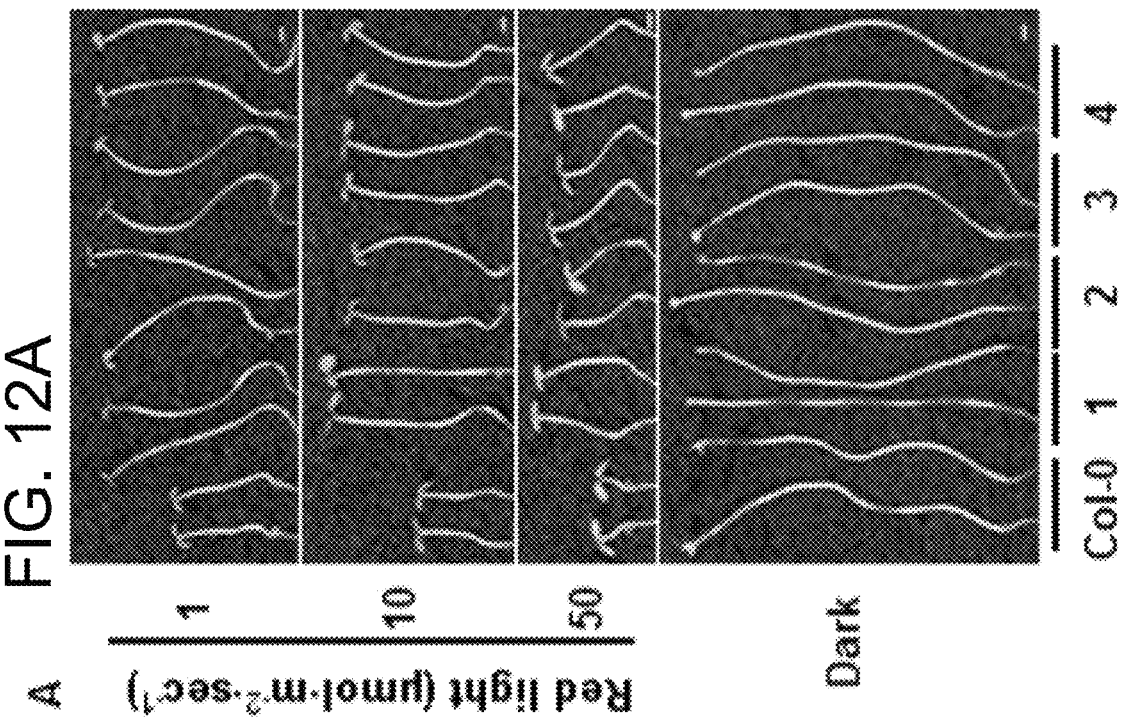

FIGS. 12A-12B illustrate that overexpression of PEP6-32 resulted in a red light insensitivity phenotype. FIG. 12A: Hypocotyl elongation of Col-0, transgenic lines 1, 2, 3 and 4 grown on black stripe medium under red light with different fluence rates and dark condition. Shown are two representative seedlings of each genotype (n=30). FIG. 12B: Comparison of relative hypocotyl elongation in wild type, transgenic lines 1, 2, 3 and 4. The relative hypocotyl elongation is the ratio of hypocotyl length between red light and dark. The asterisk indicates a statistically significant difference from wild type (VVT, Col-0) as determined by a Student's t-test (p<0.05).

FIGS. 13A-13B are 2 bar graphs illustrating that overexpression of PEP6-32 does not alter the sensitivity to blue (FIG. 13A) and far-red (FIG. 13B) light. Comparison of relative hypocotyl elongation in four independent PEP6-32 transgenic lines and comparable controls in darkness and under various fluence rates of blue or far-red light. The relative hypocotyl elongation is the ratio of hypocotyl length between blue light or far-red and length in darkness. The asterisk indicates a statistically significant difference from non-transformed controls, as determined by a Student's t-test (p<0.05).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference, by notation in the application, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, botany, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism and its regulatory sequences.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid. The term "transgene" refers to an artificial gene which is used to transform a cell of an organism, such as a bacterium or a plant.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence. As used herein, a "transgene" refers to an artificial gene which is used to transform a cell of an organism, such as a bacterium or a plant.

As used herein, "transgenic" refers to a cell, tissue, or organism that contains a transgene.

As used herein, "isolated" means removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a CCD enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

As used herein, the term "over-expression" and "up-regulation" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially equivalent cell that is not transfected with the gene) under substantially similar conditions. Thus, to over-express or increase expression of a target nucleic acid refers to increasing or inducing the production of the target polypeptide encoded by the nucleic acid, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches. Conversely, "under-expression" and "down-regulation" refers to expression of a polynucleotide (e.g., a gene) at lower levels (producing a decreased amount of the polypeptide encoded by the polynucleotide) than in a "wild type" plant cell. As with over-expression, under-expression can occur at different points in the expression pathway, such as by decreasing the number of gene copies encoding for the polypeptide, inhibiting (e.g., decreasing or preventing) transcription and/or translation of the gene (e.g., by the use of antisense nucleotides, suppressors, knockouts, antagonists, etc.), or a combination of such approaches.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest, where the plasmid of expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *E. coli*), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same terminology is sometimes applied to the arrangement of coding sequences and transcription control elements (e.g. promoters, enhancers, and termination elements), and/or selectable markers in an expression vector.

As used herein, the term "selectable marker" or "selective marker" refers to a gene whose expression allows one to identify cells and/or whole organisms (e.g., plants) that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest. Some examples of selectable markers include genes encoding for antibiotic resistance, genes encoding for fluorescence or other detectable signal. "Detectable" refers to the ability to perceive or distinguish a signal over a background signal. "Detecting" refers to the act of determining the presence of and recognizing a target or the occurrence of an event by perceiving a signal that indicates the presence of a target or occurrence of an event, where the signal is capable of being perceived over a background signal.

The terms "native," "wild type", or "unmodified" in reference to an organism (e.g., plant or cell), polypeptide, protein or enzyme, are used herein to provide a reference point for a variant/mutant of an organism, polypeptide, protein, or enzyme prior to its mutation and/or modification (whether the mutation and/or modification occurred naturally or by human design). Typically, the unmodified, native, or wild type organism, polypeptide, protein, or enzyme has an amino acid sequence that corresponds substantially or completely to the amino acid sequence of the polypeptide, protein, or enzyme as it typically/predominantly occurs in nature.

The term "phenotype", as used herein, refers to an organism's observable traits/characteristics resulting from the organism's genetic makeup (e.g., genotype) in combination with the environment.

As used herein, the term "phenotypically homogenous" indicates that individual organisms of a group/population are phenotypically so similar as to be virtually indistinguishable. Thus, if a group of plants of the same species is a "phenotypically homogenous population", although the individual organisms in the group may have some genetic variations resulting in subtle genetic differences (in other words, they may not be genetic clones), the visible and observable phenotypes (such as color, growth rate, flowering, leaf morphology, hardiness, light sensitivity, life cycle, and the like) are essentially the same. In this way, any observed differences in phenotype in transformed individuals are more than likely associated with expression of the transgene and can be putatively attributed to the tested BARP.

As used herein, the term "library" refers to a collection of items (e.g., group of DNA sequences, peptides, group of chemical compounds, group of cells, group of organisms, etc.), where most of the individual items in the library differ from every other item (or substantially every other item; some small percentage of repeats may be unavoidable) in some aspect. For instance, in a library of peptides, each peptide in the library has a different peptide sequence (with allowances for a small percentage of randomly occurring duplicates).

The term "biologically active random peptide (BARP)" refers to a peptide fragment having a random sequence that has a biological activity, in that the peptide directly or indirectly affects a biological function. In embodiments a BARP may affect a biological function by an activity such as, but not limited to, binding an enzyme active site, blocking channels, destabilizing substrates, integrating with a biochemical or structural process, and the like. In the present disclosure, a random peptide with the potential to be biologically active is referred to as a "candidate BARP" or "potential BARP". However, such potential BARPs are also sometimes referred to herein as a BARP prior to screening for activity.

Discussion

Embodiments of the present disclosure encompass methods of identifying biologically active random peptides (BARPs) in plants, methods of screening libraries of candidate BARPs for in vivo biological activity in plants, and libraries of transformed plants expressing candidate BARPs.

Plants represent a superb system to identify novel biologically-active compounds. Being anchored to the earth and unable to move away from environmental stress, for plants, survival depends on being sensitive to environmental change and chemical signals. Plants exhibit conspicuous phenotypic and developmental plasticity, rendering them well-suited for chemical genomics approaches. However, chemical genomics methods suffer from some of the drawbacks discussed above.

The methods of the present disclosure provide an alternative parallel approach to chemical genomics in the search for new plant growth regulators and other active peptides in plants. Instead of having to grow plants and subsequently treat them with expensively synthesized chemicals (in this case, peptides), each plant can be genetically altered to produce a novel peptide that may affect its own biology. Thus, instead of applying the chemical compound and looking for an effect, the methods of the present disclosure include the creation of a population of plants where each plant makes a novel compound (e.g., a plant library), which can then be screened for effects during all stages of growth and development. In this way, the individual organism (e.g., plant) tells observers which compound promotes biological consequences.

It is not believed that the approach of preparing large numbers of transgenic whole organism libraries for exploration of random peptide effects by inducing phenotypes has been used in animals, fungi, or plants. In part this may be due to the fact that easily transformable fungi (e.g., yeast) have limited phenotypes, and organisms, such as animals, with a large number of potential phenotypes are difficult to transform. Plants are relatively easily transformed, have a wide variety of observable phenotypes, are small, and can be grown in large numbers in a relatively small area, making them good candidates for this approach. Modification to the methods and systems described herein can be made to adapt such methods and systems for use in other systems, such as fungi and animals.

Plant Systems

In embodiments, the methods of the present disclosure provide a way to screen for biologically active peptides, in planta, by producing plants, each expressing a novel, random peptide sequence, referred to as a candidate BARP. This technology can have profound effects in identification of new peptide sequences that can modulate plant growth and development and potentially find use as new, environmentally sound agricultural products, such as herbicides, fertilizers, pesticides, and the like.

The present disclosure thus provides an innovative pipeline to rapidly discover new drugs and growth regulators in planta. Generally described, the present disclosure provides methods to screen populations of any transformable organism for BARPs. Small peptides have the potential to integrate into a wide set of biological processes and thus represent good candidates for discovering new biologically active compounds. The methods of the present disclosure exploit flexibility in molecular cloning techniques and degenerate sequence amplification to produce libraries of random nucleic acid test sequences encoding potential BARPs and using these test sequences to generate populations/libraries of plants where each plant expresses a different small peptide (e.g., differing in amino acid composition and/or length).

In the libraries created in the methods of the present disclosure, one or more of the individual peptide sequences (candidate BARPs) may affect biological function (e.g., may prove to be an actual BARP) by binding to enzyme active sites, blocking channels, destabilizing structures, or any one of many other possible biological integrations. Upon identification of a new phenotype in a plant in the library, the effective BARP sequence can then be determined by isolating the DNA sequence from the plants exhibiting aberrant phenotypes, and then confirming biological effects in independently-transformed plants. This approach allows the use of BARPs to discover new regulators of plant growth and development, leading to identification of potential new high-value products to increase agricultural productivity, preferably with limited environmental impact.

Methods of Identifying BARPs in Plants

In embodiments of the present disclosure of methods for identifying biologically active random peptides (BARPs) in plants, the method first includes providing a library of test nucleic acid sequences, where the test nucleic acid sequences encode a plurality of candidate BARPs. Each test nucleic acid sequence in the library includes nucleic acids encoding a start codon, a random sequence of amino acids encoding a candidate BARP, and a stop codon. The length of the test nucleic acid sequence between the start and stop codons depends on the desired length of the encoded random sequence of amino acids (e.g., the candidate BARP), which may vary. In embodiments, the candidate BARP is from about 6 to about 20 amino acids long (e.g., a nucleotide sequence of about 18 to about 60 nucleotides in length). In embodiments, the candidate BARP may include two flanking cysteine residues to provide potential disulfide bonds, which may provide additional consistent structure and/or stability to the peptide.

In embodiments, the library of test nucleic acid sequences is made by generating a plurality of nucleic acid sequences, each encoding a core random sequence of amino acids. This can be done using methods known in the art, such as by using polymerase chain reaction (PCR) techniques to generate templates to produce random peptides when introduced via an expression system into a living cell/organism, such as a plant. In embodiments, a recombination cloning technique, such as the Gateway® cloning system, is used to generate an oligonucleotide library of test nucleic acid sequences. In embodiments, the test nucleic acid sequences described above are operatively linked between flanking sequences for recombination cloning (such as Gateway® sequences).

In some such embodiments, as illustrated in FIG. 1, the nucleic acid template used to generate PCR products includes, in sequence, a primer (e.g., the portion of the sequence under the first arrow in FIG. 1), a start codon (e.g., ATG), a sequence of nucleotides encoding a random peptide sequence (represented by "NNN . . . " in FIG. 1), a stop codon (e.g., TAG, TAA, TGA), and the other flanking primer sequence. In embodiments, such as that illustrated in FIG. 1, the test nucleic acid sequence may include a spacer codon separating the core of the random peptide sequence from the start codon (e.g., the Ala codon "GCC" in SEQ ID NO: 1, but other spacer codons may be used, such as but not limited to, codons encoding for Ala or Gly (while any amino acid may be used as a spacer, Ala and Gly are least likely to interfere with the potential activity of a candidate peptide)). In some embodiments, the test nucleic acid sequence may include nucleic acids encoding for two cysteines within or flanking the randomized core sequence. In embodiments, the encoded protein thereby includes two cysteines to provide sulfur-containing side chains, which have the ability to form disulfide bonds, which may add additional structure and internal stability to the random peptide.

In embodiments, with use of recombination cloning techniques, after building the template for PCR products as described above with the test nucleic acid flanked by the known recombination cloning sequences, the test sequences are amplified by PCR. Amplification by PCR can be done with primers corresponding to the known flanking sequence, which generates a reaction mix containing a plurality (e.g., hundreds, thousands, millions, etc.) of unique sequences, each coding for a different random peptide, each representing a candidate BARP. Each of these PCR products includes the flanking regions for cloning into recombination vectors as well as the start and stop sequences flanking the nucleotide sequence encoding the candidate BARP.

The methods of the present disclosure further include creating a library of recombination vectors from the library of test nucleic acid sequences. Each vector in the library includes a test nucleic acid sequence from the library operably linked to a nucleic acid sequence encoding a selectable marker. In embodiments, the library of test nucleic acid sequences are cloned into recombination vectors (e.g., bacterial vectors) that can be used for transforming plants (or other target organism) with the test nucleic acid sequences. In embodiments, recombination, or Gateway®, cloning techniques are used, in which the population of test nucleic acid sequences generated in the first step (e.g., with PCR methods) are moved to a plasmid, such as those useful for plant transformation. In embodiments, the test nucleic acids can first be moved into an entry vector that can then be mobilized to other plasmids, such as bacterial vectors or other plant transformation vectors. The Gateway system, or other recombination cloning techniques, facilitate creation and amplification of the random test sequences, the transfer of the sequences between vectors, plasmids, and host organisms, and the isolation of the test sequences from an organism for sequencing after screening.

The library of test nucleic acid sequences generated as described above are cloned into the vectors to form a library of recombination vectors. Using these methods, each vector in the vector library includes a test nucleic acid from the library of test nucleic acid sequences. In embodiments, the recombination vectors also include a nucleic acid sequence encoding a selectable marker operably linked to the test nucleic acid. When expressed, the selectable marker produces a detectable signal (e.g., an observable phenotype, such as antibiotic resistance, color, fluorescence, etc.). This serves to identify bacterial cells and, later, plants and/or plant cells that include the test nucleic acid sequence encoding a candidate BARP (e.g., those that have been successfully transformed). In embodiments, the selectable marker can be, but is not limited to, antibiotic resistance, fluorescence, and the like. In embodiments, more than one (e.g., two or more, three or more, and the like) selectable markers can be operatively linked to the test nucleic acid. The use of more than one selectable markers allows for confirmation of transformation and/or for confirming the presence of the test nucleic acid during different steps of the method (e.g., vectors, bacterial colonies, transformed plant cells or seeds) and/or at different stages of development (e.g., seed, seedling, growing plant). For instance, in some embodiments, the test nucleic acid may be operatively linked to a nucleic acid encoding a peptide for antibiotic resistance as well as to a nucleic acid encoding a fluorescent peptide. In embodiments, the selectable marker is antibiotic resistance. In embodiments it is kanamycin resistance. In embodiments, the selectable marker is fluorescence (such as, but not limited to, the jellyfish green fluorescent protein (GFP)). In embodiments, the recombination vectors include both antibiotic resistance and fluorescence selectable markers. Thus, for purposes of illustration, if the recombinant vectors including the test nucleic acid and both an antibiotic resistance and fluorescence selectable marker are first used to transform bacterial cells for transformation of plants, the cells can be screened by growth on plates containing antibiotic to screen for transformants including the antibiotic resistance selectable marker. For confirmation, fluorescence can also be tested. Additionally, after the transformed bacterial cells are used to transform plants (e.g., by floral dipping or other method), the transformed plants or plant cells can also be screened using one or more of the selectable markers to confirm successful transformation.

The methods of the present disclosure further include transforming a population of plants with the library of recombination vectors to form a library of recombinant plants. In order to facilitate observation of new phenotypes, in embodiments the population of plants is a phenotypically homogenous population of plants of the same species. Using a phenotypically homogenous population of plants, where the individual plants share the same phenotypes (although some genetic differences may be present), makes it easier to identify the emergence of a new phenotype in an individual of the population, where such new phenotype can be associated with the candidate BARP encoded by the test nucleic acid sequence.

Methods for transforming plants using recombination vectors are known in the art. In embodiments, bacterial vectors are used to generate the library of vectors with test nucleic acid sequences. Then these bacterial vectors are transformed into bacteria that can then be used to transform plants. In embodiments, bacterial cells are transformed with the recombination vectors, and then the competent bacterial cells (e.g., as confirmed by the presence of the selectable marker) are used to transform plants. In embodiments, the plant transformation vector is a bacterial vector for *Agrobacterium tumefaciens*. In embodiments, *A. tumefaciens* strain GV3202 is used for plant transformation. In embodiments, bacterial cells containing the vectors (and, hence the test nucleic acid encoding the candidate BARP) can be identified by the presence of the signal produced by the selectable marker (e.g., growth on antibiotic selection media, fluorescence, etc.).

In embodiments, the competent bacterial cells are used to produce a library of colonies each colony containing a test nucleic acid sequence encoding a candidate BARP. The colonies can then be used to transform a plurality of plants (e.g., a plurality of phenotypically homogenous plants of the same species, variety, cultivar, etc.) with the library of recombination vectors. Plants that have been successfully transformed are then identified by the presence of the signal produced by the selectable marker (e.g., antibiotic resistance, fluorescence, combinations of these, and the like).

In embodiments, for transformation of plants, the "floral dip" procedure, known to those of skill in the art, is used on mature plants to transfect the plants with the vectors from the transformed bacterial cells. Then, seeds can be collected from the dipped plants and screened on selectable media for the presence of the selectable marker (e.g., kanamycin resistance), indicating the presence and expression of the transgene including the test nucleic acid sequence. Seedlings can then be grown from the selected seeds and observed for divergent phenotypes. In embodiments, if more than one selectable marker is used, the seedlings may be further screened for a selectable marker (e.g., fluorescence). Successfully transformed seedlings can then be grown (e.g., in soil, sterile media, etc.). Other methods for transforming plants with recombinant vectors are known in the art and are contemplated within the scope of the present disclosure. The above methods are merely illustrative and not intended to be limiting.

Using the above methods, a library of transformed plants can be generated, where each plant includes a recombination vector from the library and thus a candidate BARP. While it will be recognized that, at each stage above involving the creation of a "library" (of test nucleic acids, of recombination vectors, of plants, etc.), it is intended that each individual of the library include a different test nucleic acid encoding a different candidate BARP, some chance duplication could occur, or a plant could, by chance, contain two recombination vectors. Thus, the terms "each" and "different" in this disclosure and the accompanying claims are not meant to be absolute, but merely to convey that, in general, the each member of the library corresponds to a different candidate BARP, with allowances for some natural duplication. Furthermore, it will be understood that, in order to screen for new phenotypes (associated with a candidate BARP) in a plant, the plants in the plant library will typically all be of the same species/variety/ecotype. This is to ensure that any variation in phenotype between plants is associated with and attributable to the presence of the BARP rather than due to another genetic difference between plants. Various plant species can be used in the methods of the present disclosure, but for purposes of illustration, the examples provided utilized *Arabidopsis thaliana*. *Arabidopsis* (due to features such as quick growth rate, well-studied genome, easily observable phenotypes, etc.) represents a good plant system for transformation, screening, and confirmation of phenotype, other plant systems can also be used for all stages, particularly for further confirmation of an observed phenotype. For instance, BARPs identified in the methods of the present disclosure in *Arabidopsis* can then be transformed into other plant systems to determine if the BARP has similar activity and phenotypic effect in other plant species. In embodiments, other plant systems for use in the methods and systems of the present disclosure include, but are not limited to, camelina and petunia.

BARP Plant Libraries

Embodiments of the present disclosure also include plant libraries made according to the methods of the disclosure described above. In embodiments, a library of transformed plants of the present disclosure includes a plurality of plants (where the plants were phenotypically homogenous prior to transformation and/or where the plants were of the same original genotype), each plant including a different recombination vector. Each recombination vector in each plant in the library includes a test nucleic acid sequence encoding a start codon, a random sequence of amino acids, and a stop codon as well as a nucleic acid sequence encoding a selectable marker operably linked to the test nucleic acid sequence. The test nucleic acid sequence in each vector, and thus in each transformed plant, encodes a different random sequence of amino acids (with exception for a small potential number of duplicates, as mentioned above).

According to methods of the present disclosure, after transformation of the plants and generation of a plant library, the library of recombinant plants is then screened for the occurrence of a new phenotype (e.g., a phenotype that is discernible from a wild type plant). With the methods of the present disclosure, the plants can be observed, and thus screened, throughout the full stages of development from seed to mature, flowering plant, through senescence. Seeds from the transformed plants are collected and stored in sets. In embodiments, the seeds may be planted and screened in various stress conditions to identify phenotypes that might not manifest under typical environmental conditions. When a new phenotype occurs in one of the recombinant plants, this indicates that the candidate BARP may be responsible for the new phenotype. In other words, the presence of a new phenotype indicates that the expressed candidate BARP may be interfering with or in some way modifying a biological process of the plant to directly or indirectly produce the new phenotype.

Examples of new phenotypes that may occur in the methods of the present disclosure may manifest as a general defect, a discrete defect, or both. In embodiments, the new phenotype is a general defect selected from, but not limited to, early plant death, "glassy" or vitrified seedlings, dwarf seedlings, slowed growth, inability to flower, and inability to set seed. In embodiments, the new phenotype is a discrete defect selected from, but not limited to, early flowering, differential leaf characteristics, differential pigmentation, arrested development, long roots, bushy growth patterns, light-insensitivity, and differential light-sensitivity.

Upon detection of a new phenotype in a plant from the library, the DNA is extracted from the plant exhibiting the new phenotype, and the sequence of the candidate BARP is determined. This can be done by known sequencing methods. In embodiments, the sequences can be isolated by PCR using the same primers used in the construction of the test nucleic acid library (e.g., Gateway sequences or other recombination cloning primers), followed by DNA sequencing.

Since it is possible that the new phenotype may be the result of some other random, naturally occurring event or T-DNA insertion, additional tests may be done before positively attributing the new phenotype to the candidate BARP. Thus, in embodiments, the association of the candidate BARP with the new phenotype is confirmed by additional testing. To verify that the candidate BARP is associated with the new phenotype, after determining the sequence of the candidate BARP, additional plants are transformed with the nucleic acid sequence encoding the BARP (e.g., according to the methods described above or other transformation methods known in the art). If the seedlings of the newly transformed plants also display the new phenotype, this recapitulation of phenotype indicates that the candidate BARP is a BARP responsible for the new phenotype.

While unlimited varieties of plants can be used with the methods described above, in embodiments, the plant is *Arabidopsis thaliana*. Embodiments described in the Examples below illustrate the methods of the present disclosure using the plant *Arabidopsis thaliana*, which have thus far resulted in the identification of several new BARPs. This confirms that the method can be successfully employed to generate libraries of candidate BARPs and to identify new biologically active peptides.

Not only do the methods of the present disclosure permit identification of novel biologically-active peptides, these newly identified peptides can be utilized in the plant industry. For instance, depending on the resulting phenotype, such peptides can be installed or applied as commercial growth regulators, developmental modifiers, new peptide-based herbicides, and the like. Such technology can reduce the use of chemical pesticides and fertilizers and provide many other desired plant features.

Plant BARPS

Embodiments of the present disclosure also include identified plant BARPs that induce a specific phenotype in plants. Although numerous BARPs have been identified, the following are representative BARP sequences that produce confirmed phenotypes.

Thus, in embodiments, the present disclosure also provides synthesized and/or isolated BARPs having a sequence selected from: SEQ ID NOs: 2, 4, 6-10, 14, 16, 19, 21, 23, 26, 28, 30, and 32. The present disclosure also provides recombination vectors including a nucleic acid sequence encoding a BARP having a peptide sequence selected from: SEQ ID NOs: 2, 4, 6-10, and 14, 16, 19, 21, 23, 26, 28, 30, and 32. In embodiments, the BARP is operably linked with a promoter sequence to drive expression of the BARP in a host plant. In embodiments, the BARP is operably linked with a selectable marker for identification of plant cells, seeds, seedlings, or plants expressing the BARP.

Embodiments also include methods of conferring a desired phenotype in a plant or population of plants by transforming the plant with a specific BARP capable of inducing the phenotype, or otherwise introgressing the BARP into the plant genome. Embodiments include methods of providing plants having purple pigmented seed pods by transforming the plant with a sequence encoding a BARP having SEQ ID NO: 2 (see Example 2). Embodiments include methods of providing plants having a bushy seedling phenotype by transforming the plant with a sequence encoding BARP having SEQ ID NO: 3 (see Example 2). Embodiments include methods of providing plants having a phenotype characterized by aberrant seedlings by transforming the plant with a sequence encoding a BARP having SEQ ID NO: 4 (see Example 2). Embodiments include methods of providing plants having an early flowering phenotype by transforming the plant with a sequence encoding a BARP having SEQ ID NO: 6 (see Examples 2 and 3). Embodiments include methods of providing plants having a phenotype characterized by large, flat leaves and small petioles by transforming the plant with a sequence encoding a BARP having a sequence selected from SEQ ID NO: 7 and SEQ ID NO: 8 (see Example 2). Embodiments include methods of inducing early death and/or arrested plant growth in a plant by transforming the plant with a sequence encoding a BARP having SEQ ID NO: 9. Embodiments include methods of providing plants salt resistance and elongated root growth (see Example 2) and/or red light insensitivity (see Example 3) by transforming the plant with a sequence encoding a BARP having SEQ ID NO: 10. Embodiments include methods of inducing small rosette diameter (5 mm to 10 mm) by transforming the plant with a sequence encoding a BARP having one of SEQ ID NOs: 14, 16, 6, 19, 21, 23, 26, 28, 30, and 32 (see Example 3). Other embodiments include methods of inducing a sucrose dependent phenotype by transforming the plant with a BARP having SEQ ID NO: 14 (see Example 3).

In embodiments of the above methods, the plant is any plant species where the phenotype associated with the BARP is desired. In embodiments, the plant is *Arabidopsis thaliana*. In embodiments, the plant is transformed with a vector including the target BARP operably linked to a promoter sequence and/or a selective marker. The methods, systems, and BARPs of the present disclosure provide new ways to modify plant growth and development and introduce new and useful plant phenotypes. The methods of the present disclosure described above can be adapted for application to other transformable organisms.

In addition, embodiments of the present disclosure also include transgenic plants that produce a non-native biologically active random peptide (BARP) of the present disclosure, such as, but not limited to, a BARP having a sequence selected from: SEQ ID NOs: 2, 4, 6, 7, 8, 9, 10, 14, 16, 19, 21, 23, 26, 28, 30, and 32.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. Publications are incorporated by reference only where indicated by notation in the text, such references are incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Example 1

In the present example, the methods of the present disclosure were used to generate a library of test nucleic acids encoding a plurality of candidate BARPs, each having a core 6 amino acid random peptide sequence flanked by two cysteine residues. The sequences were also flanked by start and stop codons and Gateway® sequences, such as illustrated in FIG. 1. PCR was used with primers corresponding to the known Gateway flanking sequences to generate the test nucleic acid library. The oligonucleotides were then cloned into bacterial vectors including genes for kanamycin resistance to create a recombination vector library. The vectors were then moved to Agrobacterium tumefaciens strain GV3202 and used to transform Arabidopsis thaliana plants. Seeds were collected from the transformed plants and used to grow new plants. These plants were observed from seedling through the plant lifecycle and observed for new phenotypes. Several new phenotypes emerged, DNA was extracted from the plants displaying new phenotypes, and the sequence of the candidate BARP from the plants was determined. The procedures and results are described in detail below.
Materials and Methods The test nucleic acid sequences were synthesized using conserved initiator and terminator sequences flanking 18 random nucleotides, which provides a peptide that is ten amino acids long, with six of the core amino acids randomized, following a Met-Ala-Cys and ending with a Cys-term. This template is illustrated in FIG. 1. In the present example, the corresponding nucleic acid sequence was ATGGCCT-GTNNNNNNNNNNNNNNNNNNTGTTAG (SEQ ID NO: 5; nucleotides 14-46 of SEQ ID NO: 1). The cysteine residues in this case provide potential for formation of disulfide bonds that may impart additional structure to the adjacent amino acid loop. Although in this example 18 random nucleotides (identified as "N" in SEQ ID NOs: 1 and 5) were used, any number may be used, as long as it is a multiple of three.

To construct the library of random-core BARP sequences, the above DNA sequence was synthesized as an oligonucleotide sequence, along with flanking sequences corresponding to the Gateway® recombination sequences. The middle portion of the sequence, represented by "N" in FIG. 1, were randomized nucleotides. Known synthesis techniques were used to build the sequences, resulting in a library of PCR products containing test nucleic acid sequences (start codon, spacer codon, cysteine codon, 18 random nucleotides encoding a core candidate BARP sequence, second cysteine codon, and stop codon) flanked by Gateway recombination sequences. Although Gateway® sequences were used in the present examples, other recombination cloning primer sequences could be used or specifically designed.

The library of PCR products containing random test sequences was amplified using PCR based on flanking primers containing Gateway recombination sequences. These reactions produced a population of PCR products each containing the core peptide test sequence flanked by Gateway recombination sequences. These PCR products were introduced to the vector pDONR222 using Gateway recombination, and then transformed into E. coli genotype DH5α. The transformation vector also included the NPTII gene for kanamycin resistance. The E. coli cells were plated on kanamycin plates at low density to obtain single-colony separation. The single colonies each contained a separate plasmid bearing a random peptide sequence.

The colonies were recovered from plates in liquid medium, and the plasmids were isolated. The isolated plasmids represented a library of many independent, random sequences (encoding candidate BARPs) flanked by 'start' and 'stop' sequences. This library was then mass transformed into the plant overexpression vector pK7WGD2, containing selectable markers for spectinomycin in bacteria and kanamycin in transformed plants, using the LR Gateway reaction, such that each plant expression vector contained a separate test sequence (encoding a candidate BARP), and the recombinant plasmids were transformed into E. coli DH5 α cells. The cells were then plated to single-colony resolution. The colonies, each representing a different test sequence, where then harvested in liquid medium and plasmids were isolated. The plasmid population represented a non-homogenous series of plasmids, each containing a plasmid containing selectable markers and a unique DNA sequence encoding a candidate BARP flanked by regulatory sequences to drive its expression in planta. The plasmids were then transformed into Agrobacterium tumefaciens strain GV3101 and then plated en masse on LB medium containing spectinomycin for selection of positive transformants. The resulting cells were then used to transform Arabidopsis thaliana plants by floral dipping, using methods known to those of skill in the art.

Seeds from transformed plants were harvested four weeks after floral dipping and were plated to 1× Murashige and Skoog media containing 50 mg/L kanamycin for selection of positive transformants. The plates were stratified for 48 hours at 4° C., and then were placed at 22° C. for ten days. Seedlings were screened for kanamycin resistance and/or GFP, indicating successfully transformed plants. GFP-positive/kanamycin resistant plants were scored for phenotypes from first emergence through maturity and into flowering and senescence. Representative examples of some observed phenotypes associated with the inserted BARPs are presented in Table 1, below, but many more BARP associated phenotypes have been observed/identified using these methods.

As described in more detail in Example 2, below, confirmation of phenotype was performed by isolating BARPs from plants exhibiting new phenotypes and transforming into independent lines to confirm phenotype.

Also, to test for phenotypes not readily observable under normal conditions, seeds were collected from all plants in sets of nine and stored together, then planted and screened in various stress conditions (such as salt media, water-deficit, and the like), as described in greater detail in Example 2, below.
Results and Discussion Using the above procedures, a library of over 1000 transgenic plant lines, each producing a random peptide (candidate BARP), were produced. The results demonstrated a remarkable display of new phenotypes. Approximately 15% of plants in the library exhibited a new phenotype, presumably caused by the inserted peptide.

The first plate of several hundred seeds produced thirteen transformants, four of which maintained discernible phenotypes. Subsequent screens produced many more new phenotypes. Although hundreds of the resulting seedlings displayed no immediate impairment, approximately 15-20% of the seedlings exhibited a clear defect. Plant husbandry procedures were altered slightly, as it was noted that some plants with new peptides were frail and did not survive well in soil for long enough to fully observe the characteristics of a new phenotype. Thus, care of the compromised seedlings was modified in order to allow them to grow to the point where tissue could be harvested for analysis and DNA extraction to determine the sequence of the BARP presumptively affecting the plant growth. For instance, strongly affected seedlings were transferred to sterile medium with complete nutrients and sucrose as a carbon source. These conditions allowed some of these plants to develop to the point where DNA could be prepared to isolate the effective BARP sequence.

Figure 2C:
FIG. 2A-C are digital images illustrating several observed phenotypes induced by random peptides according to embodiments of methods of the present disclosure.
Figure 2B:
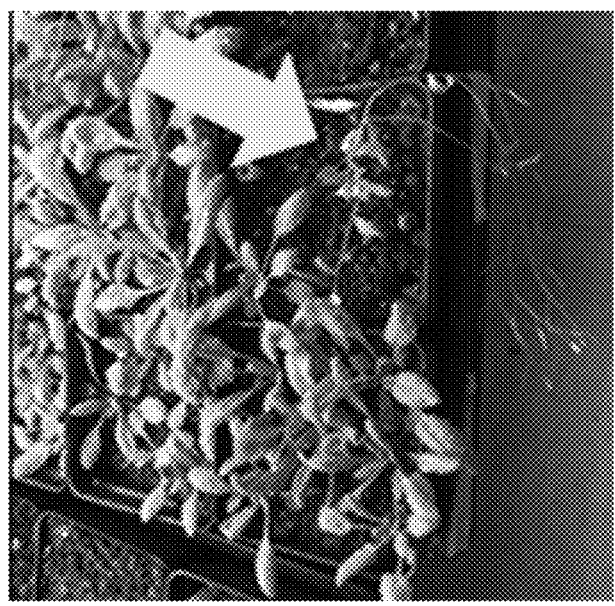
Figure 2A:
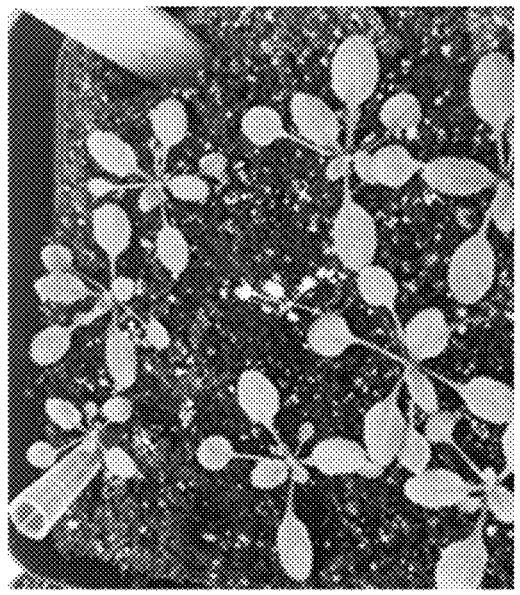

Among all the various observed phenotypes, two exemplary classes of effects were observed, general and discrete defects. Some of the observed phenotypes are illustrated in the images shown in FIGS. 2A-2C. As shown in the figures, three of the observed phenotypes included reduced or stunted growth and development (followed by death) (FIG. 2A), early flowering and seed production (FIG. 2B), and reduced size and aberrant leaf production (FIG. 2C).

Figure 3C:
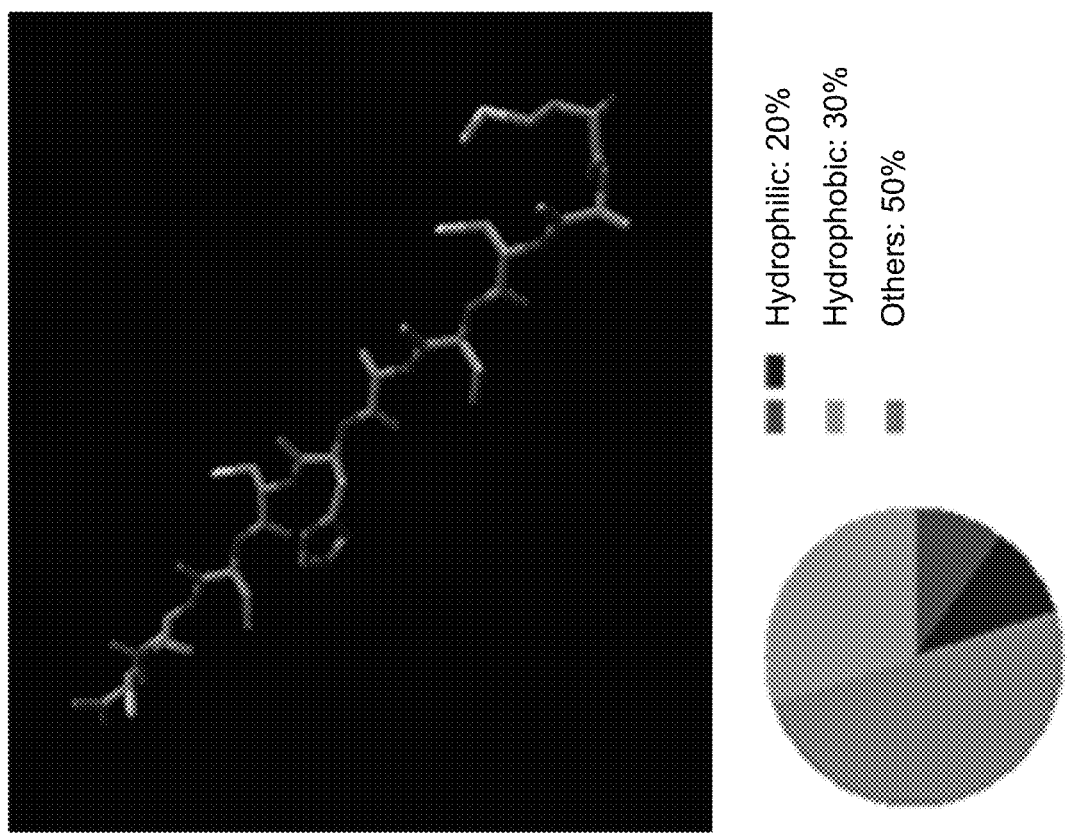

The sequences corresponding to three of the elucidated BARPs and predicted peptide structure and peptide characteristics are shown in FIGS. 3A-3B. SEQ ID NO: 2 was associated with hyperaccumulation of purple pigments in seed pods (FIG. 3A). The BARP of SEQ ID NO: 3 (FIG. 3B) resulted in a "bushy" seedling with small and upright leaves. Another BARP (SEQ ID NO: 4) was isolated from plants exhibiting aberrant seedling characteristics (FIG. 3C). Some peptide characteristics (e.g., percent hydrophilicity and/or hydrophobicity) of the three BARPs are provided in the pie chart below each structural model in FIGS. 3A-3C.

The two general classes of defects observed were general defects and discrete defects. Phenotypes involving general defects were observed with high frequency and no clear association with a specific aspect of the sequence was determined. The defect may arise from a general characteristic of the peptide that may be shared by many different peptides in the population, or potentially from high levels of expression that affect the plant promiscuously. For instance, it is possible that a group of six hydrophobic residues might force associations with membranes that render them unstable. Several general defect phenotypes were observed at a high frequency: a. Herbicidal (plant death after a developmental stage, typically upon emergence of the first true leaves), b. "Glassy" seedlings (edema, poor performance, vitrified and appear clear, green and disorganized), c. Dwarf seedlings (small stature, possibly from pleiotropic effects), and d. Episodic Performers or "underperformers" (develop slowly, although viable may not flower and produce seed, often revert, partially or completely, with age). Examples of some such observed defects, such as early death, dwarf seedlings, etc. are listed in Table 1, below illustrating the variety of observed phenotypes associated with the expressed BARPs.

The second class of defects observed was discrete defects. The discrete defects have a specific phenotype and clearly appear to be due to the inserted peptide sequence. After screening thousands of seedlings, a substantial number of discrete defects were observed. Examples of observed discrete defects included early flowering, atypical leaves, pigment accumulation, developmental arrest, long roots, bushy growth habits, light insensitive behavior, and many others (Table 1).

Upon observation of a new phenotype, DNA was isolated from a 1 mm×1 mm piece of leaf tissue. The DNA was isolated and the region encoding the BARP was identified and amplified using the same primers used in the PCR library generation. The sequence of the BARP associated with the new phenotype was thus determined, such as the BARP sequences illustrated in FIGS. 3A-3C (SEQ ID NOs: 2-4).

Determining the identity of the sequence of the BARP in the plant with the new phenotype allows independent verification of the BARP phenotype by separately transforming new plants with the BARP sequence to determine that the observed phenotype is repeated in the new plants, thus indicating the BARP is responsible for the new phenotype. While it is possible that the BARP produces the effect in the plant, it is also possible that the plant defects are not due to the sequence of the novel, random peptide, but instead due to non-specific causes, such as collateral effects of genomic integration (e.g., random location of insertion of the BARP into the host genome). It is believed that the latter possibility is unlikely because most plants have at least two copies of every gene. However, verification of the phenotype in new plants further reduces, or eliminates, the likelihood that the phenotype is due to something other than the information in the inserted sequence.

Cases were identified where the installed sequence led to poor plant performance and death, and in some of these cases, the installed sequence does not encode a full-length peptide due to a termination codon in the second place in the sequence. However, the randomly-generated sequence that caused plant death matched well to a suite of plant coding sequences in the anti-sense orientation, suggesting it may be playing a role in RNAi-based removal of a large suite of necessary plant transcripts. These findings suggest that the sequences also can have effects as active RNA species, not just peptides.

Example 2

Independent Replication of Peptide-Induced Phenotypes

A number of first-transformed generation plants were prepared and phenotypes were observed using the methods described in Example 1, above. In this example some 12-amino-acid-long candidate BARPs were also synthesized and tested. The procedures were the same as for the 6-aa BARPs described in Example 1. These phenotypes were also observed to be stable and inherited in subsequent generations. To verify that the effects observed are due to the expressed peptide and not to other less-likely positional/insertional causes, in this Example, a substantial number of the of the candidate 6 and 12 amino-acid-long BARPs were sequenced and separately transformed into independent plants. The number of independent transformants tested is shown in Table 1.

Also, to test for phenotypes not readily observable under normal conditions, seeds were collected from all plants in sets of nine and stored together, then planted and screened in various stress conditions to identify additional phenotypes. For example, seeds were planted on plant-growth media containing 100 µM NaCl to screen for seedlings showing resistance to salt. Populations of BARP containing plants have also been grown in soil under water-deficit stress, leading to identification of peptides that confer tolerance to drought stress up on further evaluation.

Materials and Methods

DNA was extracted from plants exhibiting new phenotypes by heating a 1 mm$^{-2}$ piece of the tissue to 95° C. for 10 min in a thermalcycler in 50 μl of a buffer containing 10 mM Tris-HCl (ph 8.1), 50 mM KCl and 1 mM EDTA. One microliter was used in a PCR reaction under standard conditions, and using primers corresponding to the attachment (recombinational cloning sequences) of the Gateway vector, the corresponding BARP sequences was amplified. This sequences were then recombined into the pDONR222 vector and then re-ligated into the binary pKWDG2 overexpression vector as described above. This sequence was then re-introduced into *Arabidopsis thaliana* plants using the floral dipping strategy and selection as noted above. The seedlings were then analyzed for the phenotype as defined by the original transformant. Recapitulation of the phenotype in multiple, independent transformation events provided high evidence of a specific physiological effect of the peptide.

To test for phenotypes related to salt tolerance, seeds were planted on plant-growth media containing 100 μM NaCl to screen for seedlings showing resistance to salt.

Results and Discussion:

The results described here and in the associated figures (FIGS. 4-7) demonstrate that some observed phenotypes were reproducible phenotypes and were observed in independent transformations.

Figure 4B:
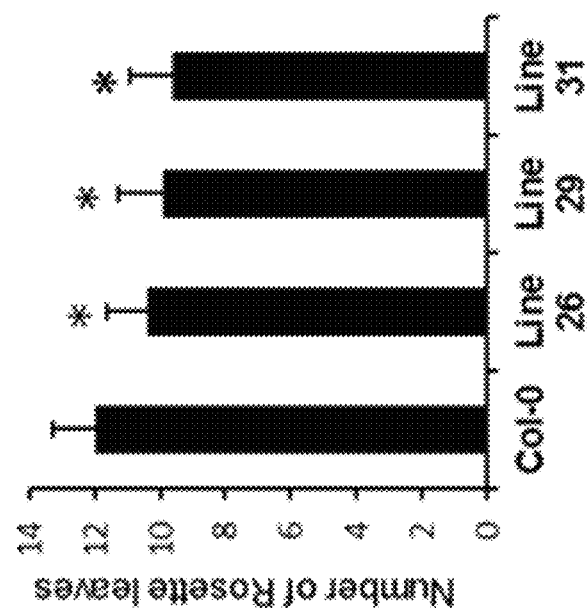
FIGS. 4A-4B illustrate early flowering behaviors of transformed plants expressing the BARP named 6AA-15 (SEQ ID NO: 6).
Figure 4A:
Figure 4C:
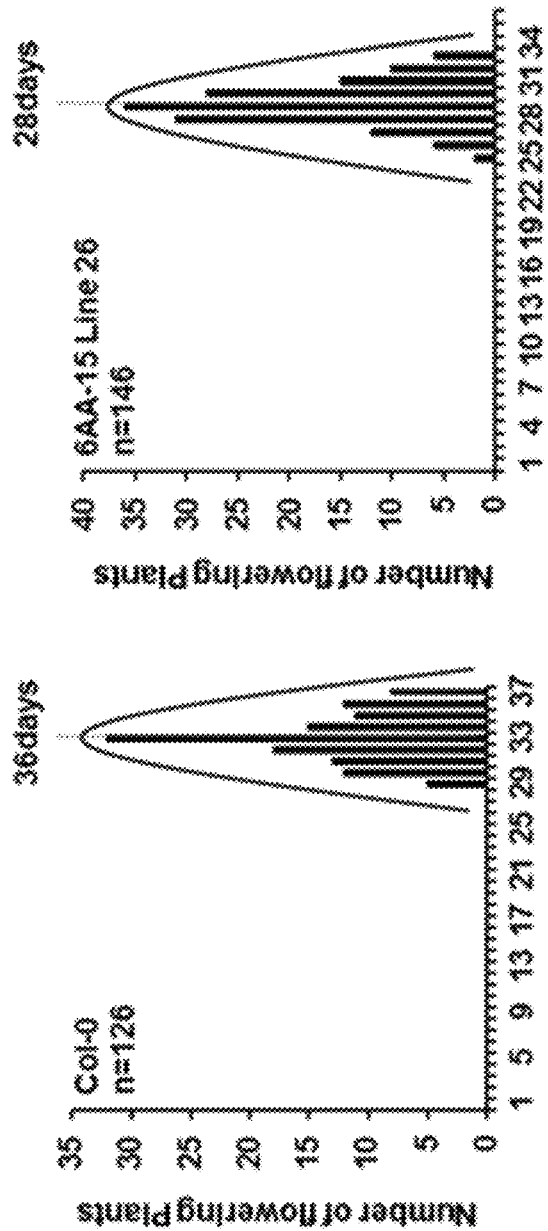
FIGS. 4C-4F are a series of graphs illustrating quantitative analysis of flowering time for the plant lines illustrated in FIG. 4A, with a minimum of 113 plants analyzed per line.
Figure 4D:
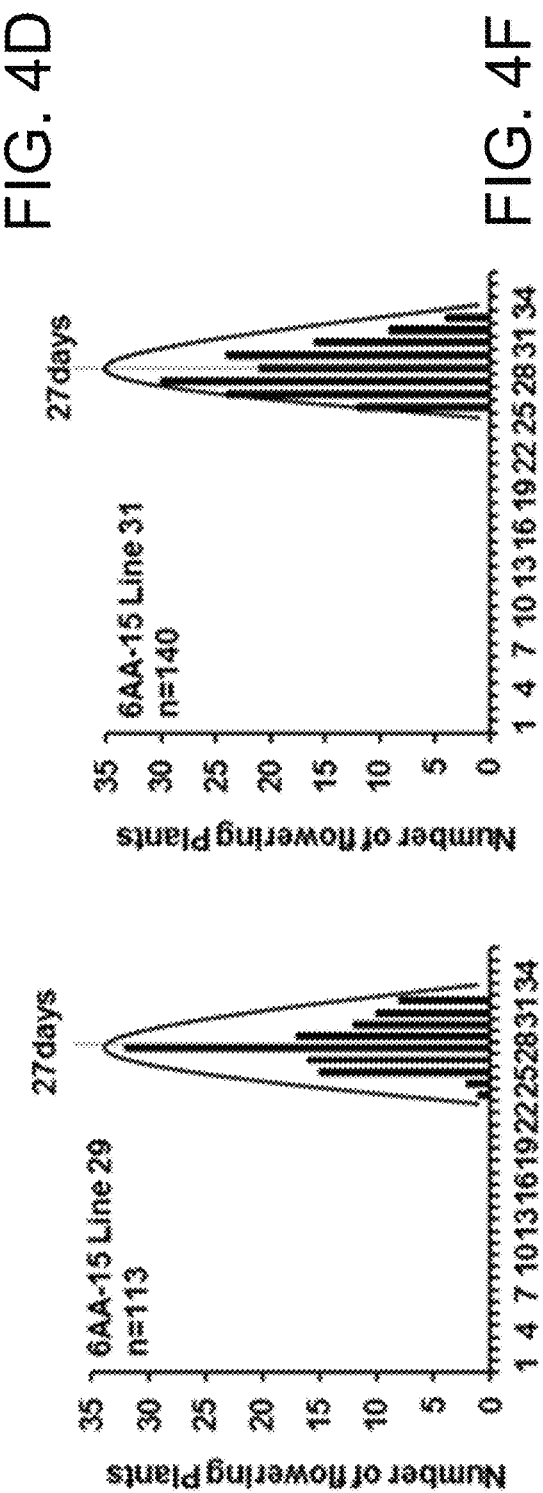
Figure 4E:
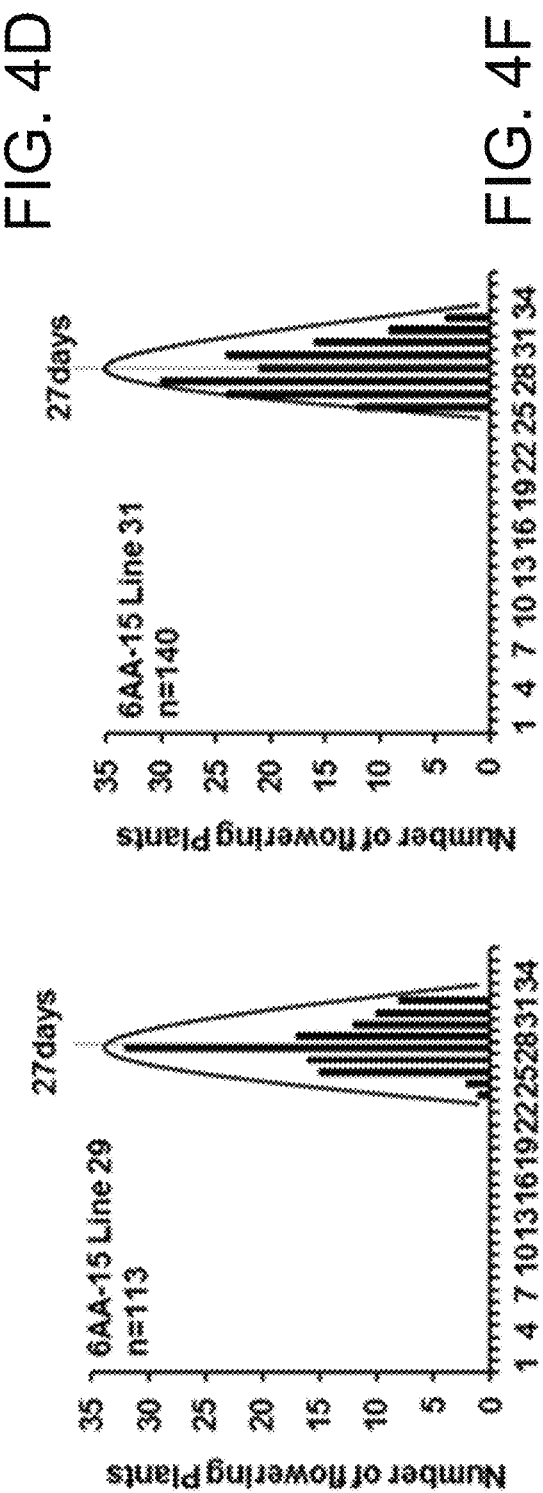
Figure 4F:
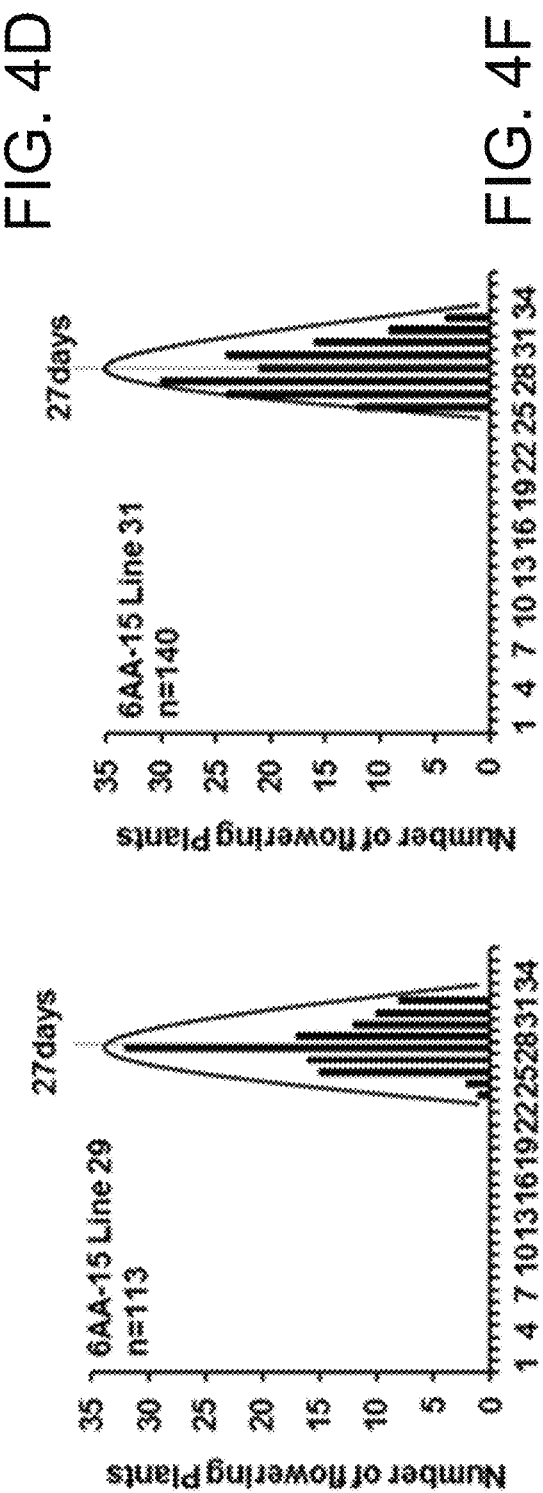

The first is a construct known as CBF6AA-15, which confers early flowering behaviors and having the sequence MACDFNFGIC (SEQ ID NO: 6). Three independent transformant lines (26, 29, and 31) are shown, and all reflect a significant early-flowering phenotype, both in days until flowering and fewer leaves at flowering as illustrated in the digital image shown in FIG. 4A. The observed phenotype was also confirmed by the observed number of rosette leaves present on the plant at the time of flowering, where transformants flowered days earlier and after producing fewer leaves. As illustrated in FIG. 4B, all three plants transformed with the CBF6AA-15 BARP had a fewer number of leaves at the time of flowering than the wild type (Col-0), also indicating early flowering phenotype. A minimum of 113 plants were analyzed per line, and the number of days until flowering was recorded. FIGS. 4C-4F illustrate the distribution of flowering times of wild type plants vs. the three transformant lines, with the mean shifting from 36 days in wild-type plants to 27028 days in the transgenic lines.

Figure 5A:
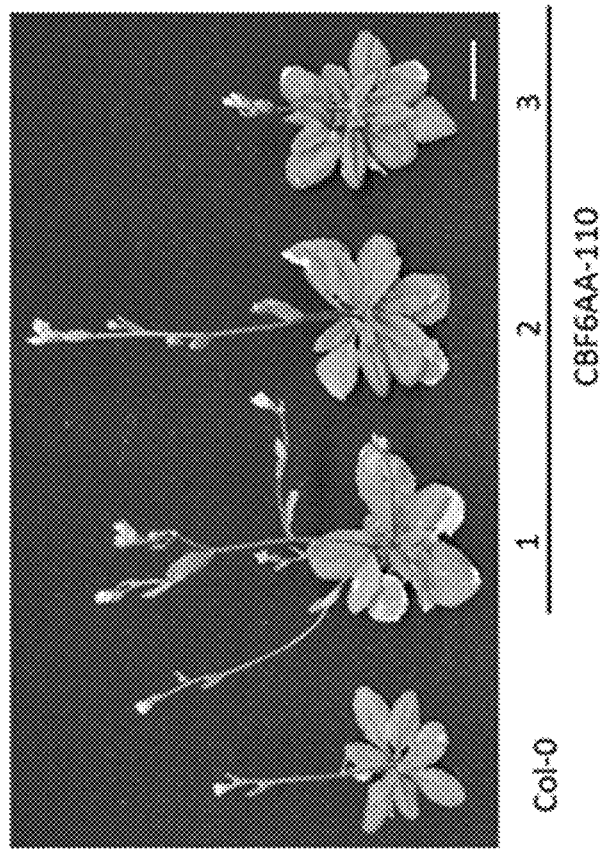
FIGS. 5A-5B illustrate the observed phenotype of plant size and leaf shape for two different BARPS, 6AA-85 (SEQ ID NO: 7) and (SEQ ID NO: 8), with three independent lines tested for each BARP.
Figure 5B:
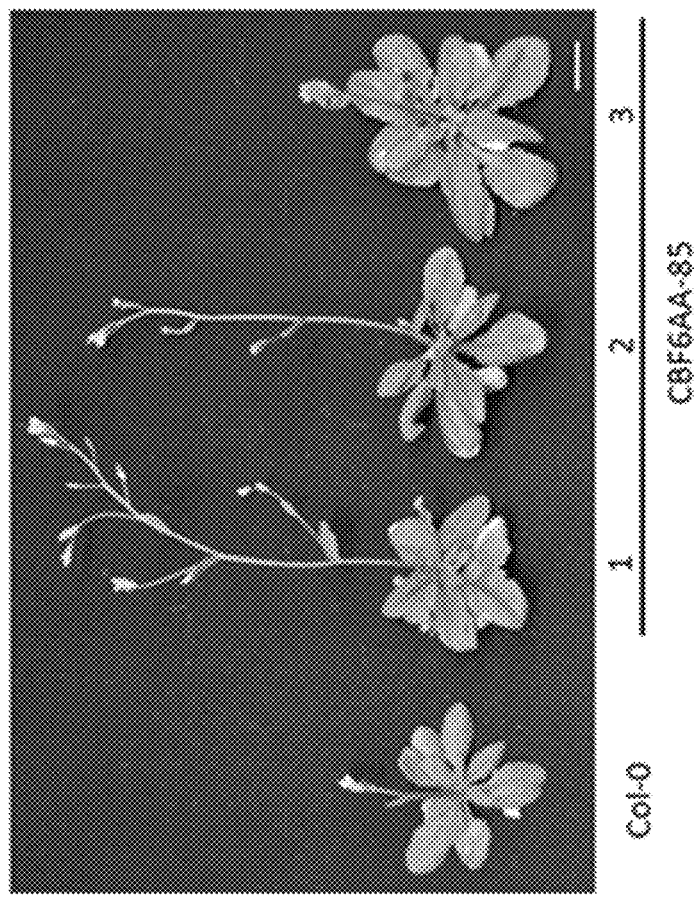

Two other BARPs induced large, flat leaves with small petioles that are different from wild type. The peptides, named CBF6AA-85, having sequence MACKQAXQRC ((SEQ ID NO: 7), where "X" represents a stop codon, and CBF6AA-110, having sequence MACWTSSVLC (SEQ ID NO: 8), show similar effects, yet are different peptide sequences. These effects were also confirmed in 3 independent lines as illustrated in FIG. 5A (for CBF6AA-85) and FIG. 5B (for CBF6AA-110).

Figure 6C:
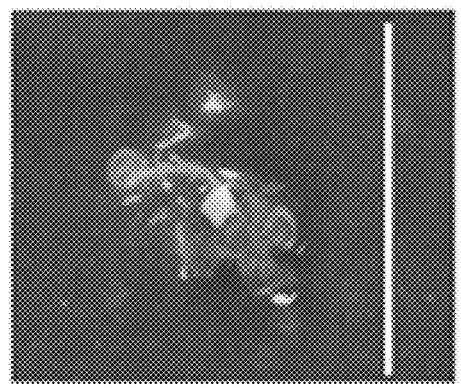
FIGS. 6A-6C are digital images illustrated the arrested plant growth phenotype resulting from the 12 amino acid BARP 12AA-97.
Figure 6B:
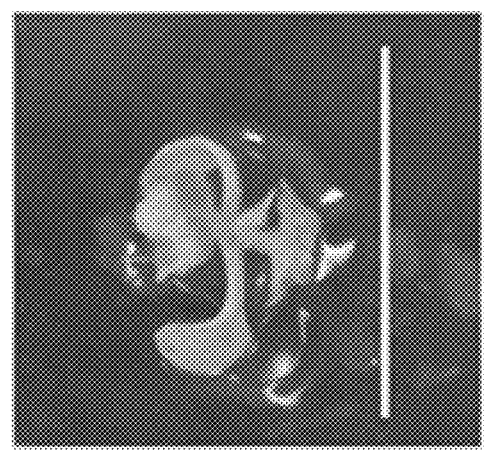
Figure 6A:
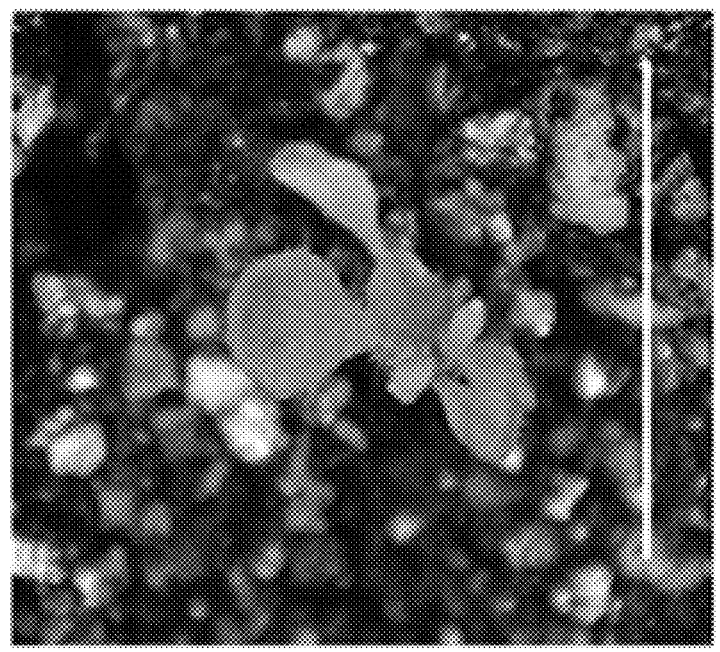

Several 12 amino acid long BARPs were also prepared and tested as described above. Several produced observable phenotypes. One of these, BARP 12AA-97, having sequence MGCVCIEPYQRLRAKC (SEQ ID NO: 9) resulted in arrested plant growth in independent lines. These seedlings never grew past the emergence of the first leaves, even in accommodating culture conditions as illustrated in FIGS. 6B-6C. This 12 amino acid sequence is being further tested for herbicidal activity when applied to the plant.

Figures 7A, 7B:
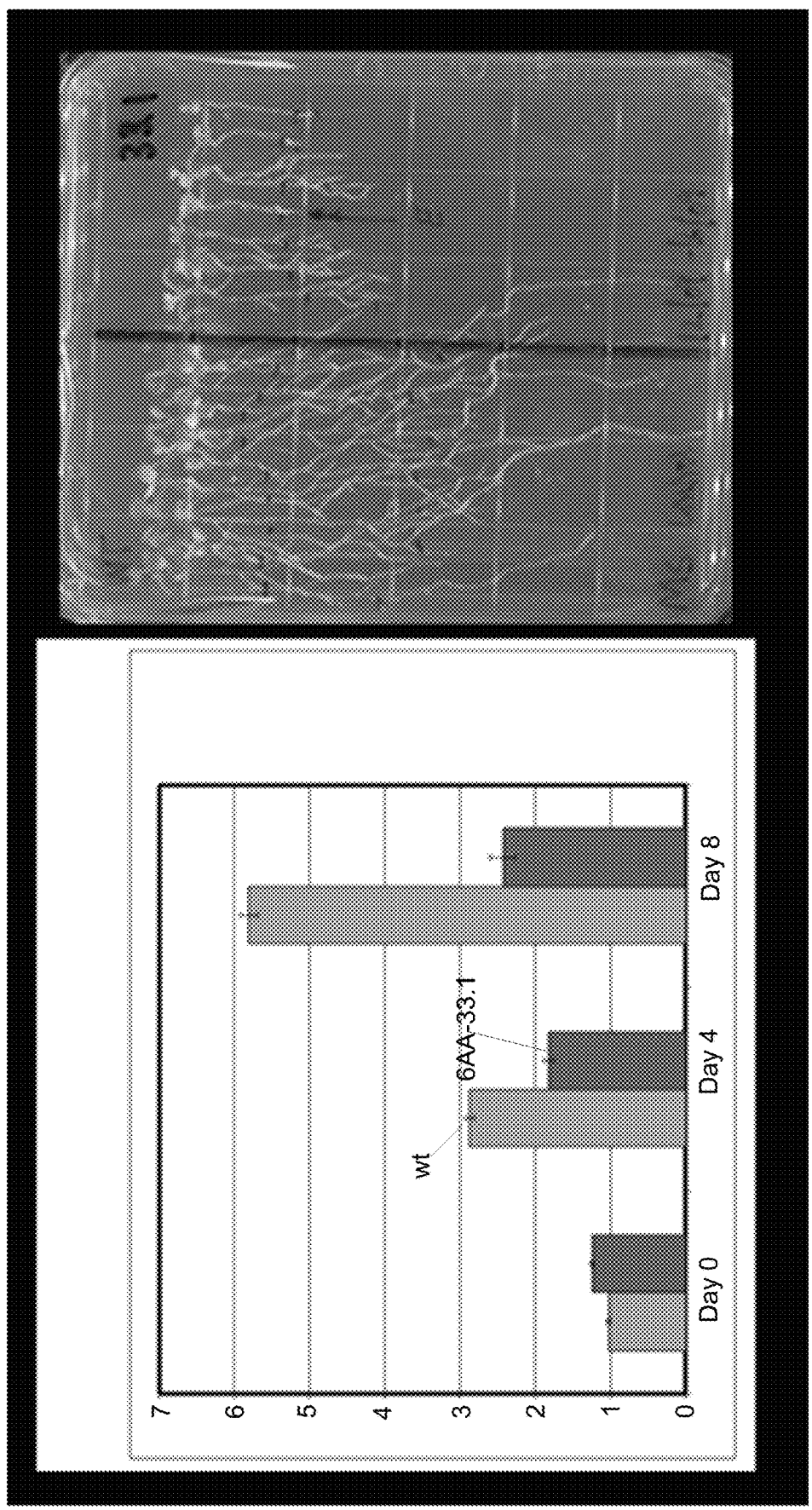
FIGS. 7A-7B illustrate a salt tolerant and root growth phenotype observed from peptide BARP 6AA-33.1.

Also, to test for phenotypes not readily observable under normal conditions, seeds were collected from all plants, stored, and later planted and screened in various stress conditions to identify additional phenotypes. In one example, seeds were planted on plant-growth media containing 100 μM NaCl to screen salt tolerance. Two lines thrived on the high-salt media, one of them resulting in a conspicuous root phenotype. The peptide, BARP 6AA-33.1, having sequence MACPASVSVC (SEQ ID NO: 10) was grown on salt media, and showed both salt tolerance as well as a root growth phenotype, as illustrated in FIGS. 7A and 7B. The transformed showed both improved resistance to salt stress as well as exhibiting alterations in root elongation. The left-hand bars in the graph in FIG. 7A represent wild-type seedlings, and the right-hand bars show the effect of the peptide. Root elongation was measured four days after germination (Day 0) and then again at four-day intervals. Error bars represent standard error of the mean. FIG. 7B shows a sample of one representative experiment, where seedlings were grown on vertical agar plates under light, demonstrating the increase in root elongation in the BARP 6AA-33.1 transformants (right) compared to wild-type seedlings (left).

Populations of BARP containing plants have also been grown in soil under water-deficit stress, leading to identification of peptides that confer tolerance to drought stress up on further evaluation. Many additional conditions, such as survival of cold, heat, darkness, and other stressors continues going forward.

TABLE 1

| BARP | phenotype | No. of independent transgenic lines |
|---|---|---|
| 6AA-3 | tiny, less seeds | 21 |
| 6AA-12 | tiny, less seeds | 9 |
| 6AA-15 | tiny, slightly early flowering | 13 |
| 6AA-16 | small, early flowering | 1 |
| 6AA-24 | tiny | 10 |
| 6AA-30 | tiny | 9 |
| 6AA-37 | tiny, abnormal leaf shape | 9 |
| 6AA-41 | drought tolerant | 5 |
| 6AA-48 | drought tolerant | 14 |
| 6AA-56 | tiny, curly leaves | 4 |
| 6AA-72 | no seeds | 5 |
| 6AA-77 | tiny, abnormal leaf shape | 5 |
| 6AA-79 | tiny, died early | 1 |
| 6AA-80 | tiny, died early | 4 |
| 6AA-85 | tiny, curly leaves | 4 |
| 6AA-91 | big | 5 |
| 6AA-106 | tiny | 3 |
| 6AA-107 | tiny | 10 |
| 6AA-108 | tiny | 2 |
| 6AA-110 | tiny | 7 |
| 6AA-111 | tiny | 9 |
| 6AA-121 | tiny, less seeds | 2 |
| 6AA-136 | tiny | 8 |
| 6AA-142 | early flowering | |
| 6AA-15X | tiny, died early | 3 |
| 6AA-156 | big, late flowering, drought tolerant | 6 |
| 6AA-164 | big, late flowering | 5 |
| 6AA-177 | small, less seeds | 6 |
| 6AA-213 | small, died early | 4 |
| 6AA-222 | early flowering | 1 |
| 6AA-224 | died early | 4 |
| 6AA-226 | big, late flowering | 7 |
| 6AA-261 | small | 9 |
| 6AA-265 | tiny | 1 |
| 6AA-285 | early senescence | 5 |

TABLE 1-continued

| BARP | phenotype | No. of independent transgenic lines |
|---|---|---|
| 6AA-305 | late flowering | |
| 6AA-371 | died early | |
| 6AA-391 | late flowering | 1 |
| 6AA-428 | late flowering | 4 |
| 6AA-469 | small, early flowering | 2 |
| 6AA-480 | small, early senescence | 1 |
| 6AA-483 | tiny | |
| 6AA-501 | multiple shoots | 1 |
| 6AA-518 | big | |
| 6AA-669 | tiny | |
| 6AA-703 | dark green, short inflorescence | |
| 6AA-718 | died early | |
| 12AA-97 | died late | 2 |

References for Examples 1 & 2

1. Spring D R (2005) Chemical genomics: Small molecules offer big insights. Chem Soc Rev 34:472-482.

2. Higashigmia T, et al. (1988) Mastoparan, a peptide toxin from wasp venom, mimics receptors by activating GTP-binding regulatory proteins. J. Biol. Chem. 263, 6491-6494.

3. Abdiche, Y., et al., 2008. Determining kinetics and affinities of protein interactions using a parallel real-time label-free biosensor, the Octet. Anal. Biochem. 377: 209-217.

4. Alonso, J. M., et al., 2003. Genome-wide insertional mutagenesis of *Arabidopsis thaliana*. Science 301: 653-657.

5. Yamada, K., et al., 2003. Empirical analysis of transcriptional activity in the *Arabidopsis* genome. Science 302: 842-846.

6. Estevez, J. M. and C. Somerville. 2006. FlAsH-based live-cell fluorescent imaging of synthetic peptides expressed in *Arabidopsis* and tobacco. BioTechniques 41: 569-70, 572.

Example 3

Identification of Novel Growth Regulators in Plant Populations Expressing Random Peptides In the present example, ten and sixteen amino acid sequences, bearing a core of six and twelve random amino acids, have been synthesized in *Arabidopsis thaliana* plants similar to Example 1. Populations were screened for phenotypes from seedling stage through senescence. Dozens of phenotypes were observed in over 2000 plants analyzed. Ten conspicuous phenotypes were verified through separate transformation and analysis of multiple independent lines. The results indicate that these populations contain sequences that often influence discrete aspects of plant biology. Novel peptides that affect photosynthesis, flowering, and red light response are described. These populations serve as a new tool to identify small molecules that modulate discrete plant functions that could be later produced in transgenic plants or applied exogenously to impart their effects.

Introduction

Small peptides regulate numerous biological processes in eukaryotes. A fourteen amino-acid peptide in wasp venom influences histidine secretion by mimicking an activated G-protein coupled receptor (Higashijima et al., 1988). Mushrooms of the *Amanita* genus produce a cyclical eight-amino acid peptide that interferes with DNA-dependent, RNA polymerase II activity (Lindell et al., 1970). In plants, peptides with known signaling roles exist either as 5-20 amino acid sequences generated from post-translational processing, or cysteine-rich peptides that are generated from precursor proteins (reviewed in Breiden and Simon, 2016). Other examples from across eukaryotes show that even short runs of amino acids play important roles in an emerging suite of key biological processes.

Figure 8:
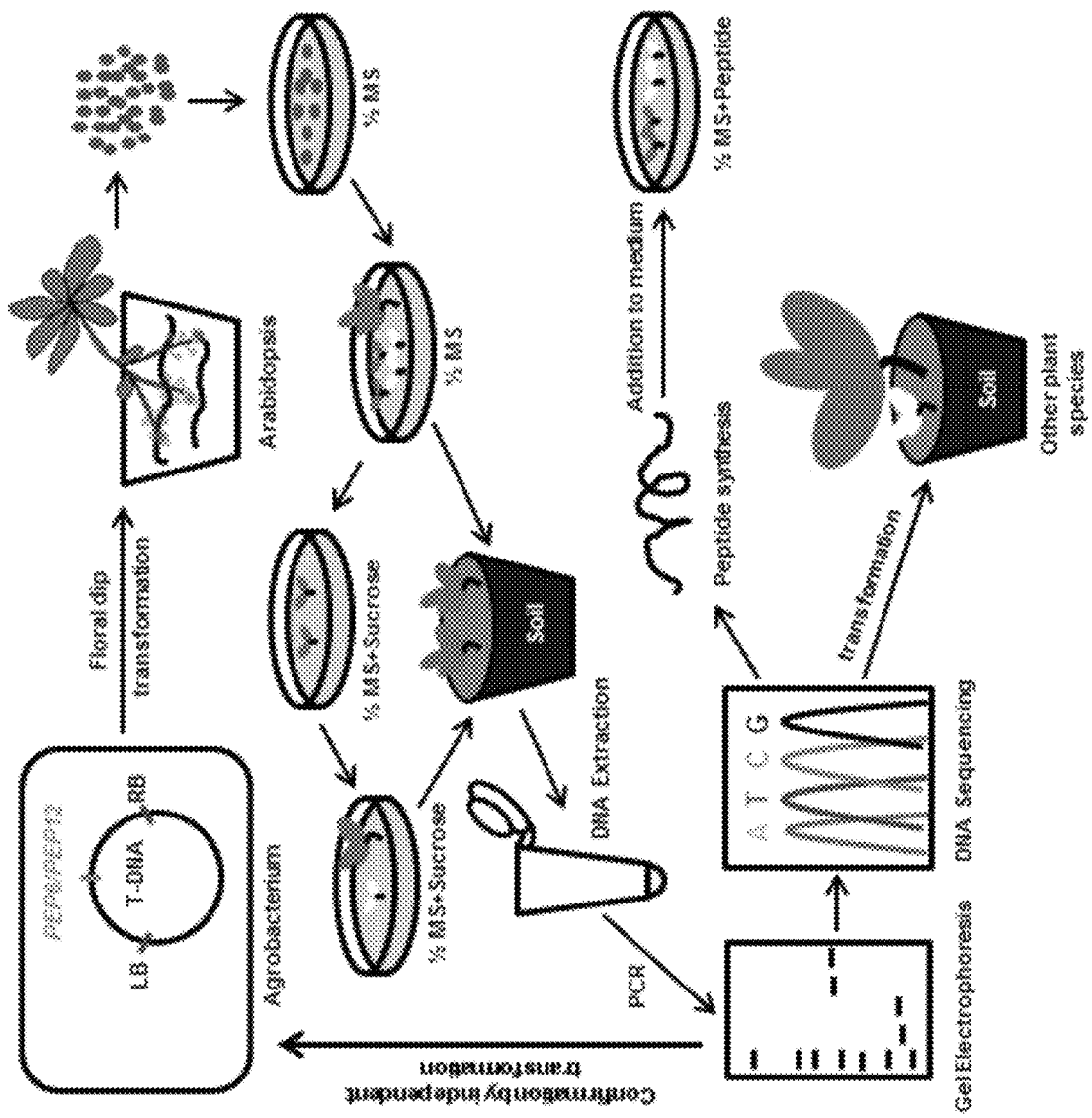
FIG. 8 illustrates a scheme for the identification of biologically-active random peptides. *Arabidopsis* plants were transformed by *Agrobacterium tumefaciens* G3101 containing a transformation vector encoding a random peptide sequence, using the floral dipping method. T1 plants were selected on ½ MS plates with kanamycin. Seedlings with true leaves were transplanted into soil, and resistant seedlings without true leaves were transferred to ½ MS plates supplemented with 2% sucrose and kanamycin. Plants rescued by sucrose were transplanted into soil. DNA was extracted from each plant and the transgene sequence was amplified using flanking primers. PCR products were sequenced by Sanger sequencing, and the same sequence was re-introduced into the transformation vector and re-introduced into *Arabidopsis* to generate independent transgenic lines. Reproducible phenotypes in different transgenic lines indicated that the phenotype was potentially associated with the rpORF. The short peptides can then be synthesized according to deduced amino acid sequence from the rpORF and applied exogenously to test for effects. Alternatively, the construct containing the rpORF may be transformed into second plant species such as petunia to test the function of rpORF.

In this and the previous Example, *Arabidopsis thaliana* plants have been developed where each plant produces a unique DNA sequence that encodes a peptide with a core of six or twelve random amino acids, flanked by cysteine residues to potentially facilitate cyclization. The transgene-bearing lines are then screened for phenotypes, either conspicuous under ambient conditions or exposed by growth in challenging conditions. Genomic DNA is then prepared from plants showing variation relative to wild-type controls, and the sequence encoding the random peptide is amplified using flanking primers. The same sequence is then re-introduced into new transgenic lines to test for recapitulation of the original phenotype. This process is illustrated in FIG. 8.

In screening a population of over 2,000 transgenic plants in the present example, dozens of phenotypes have been identified that have been reproduced in separate transformation events. These include early flowering, dwarf plants, short roots, insensitivity to red light, developmentally-timed plant death, and a variety of other phenotypes. Independent transformations have shown that the results are caused by the installed sequence, presumably due to the production of the encoded peptide.

In this example we present a new way to potentially identify novel molecules that could modulate important processes in plants. The peptides identified may then be used to impart their effects in transgenic plants or potentially even when applied in drenches or sprays. The structure of the peptides may be a basis of drug discovery, leading to new compounds (such as mimetic peptides) representing novel growth regulators, herbicides or developmental modulators.

Results

Discrete Random Sequences Induce a Range of Morphological Responses

Figure 9:
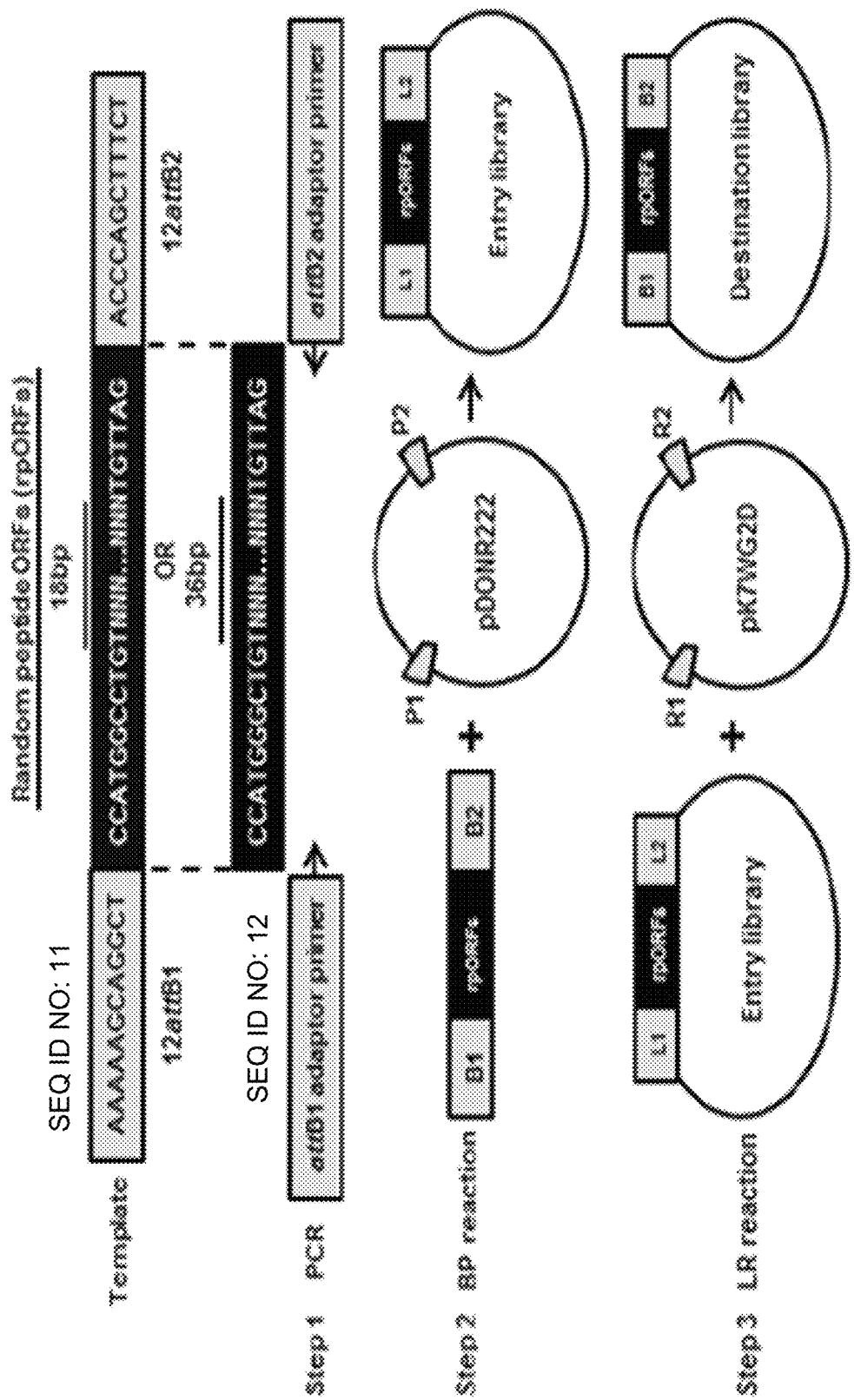
FIG. 9 is a diagram illustrating construction of random peptide ORFs expression library, including both PEP6 (SEQ ID NO: 11) and PEP12 (SEQ ID NO: 12) DNA oligonucleotides (where N can be A, G, C, or T, such that each group of three N's "NNN" encodes an amino acid).

Two libraries encoding six- and twelve-random amino acid cyclized peptides (denoted PEP6 and PEP12, respectively) were constructed in binary vectors (as illustrated in FIG. 9) using a Gateway cloning strategy and transformed into *Arabidopsis*. More than 1,500 transgenic plants with the PEP6 T-DNA inserts were isolated and more than 600 transgenic plants were isolated carrying the PEP12 insert, representing a survival ratio of 1.8% and 1.2% respectively under kanamycin selection. To ensure library representation in the population, DNA was prepared from at least fifty transgenic plants, including ten that had small rosette diameter (5 mm to 10 mm) (e.g., those having BARP sequences SEQ ID NO: 14, 16, 6, 19, 21, 23, 26, 28, 30, and 32) compared to normal-sized plants (25 mm to 30 mm; see Table 2). The nucleotide sequences of all amplified random peptide open reading frames (rpORFs) were different, indicating representation of library diversity was maintained throughout the cloning and transformation process.

Several phenotypes were visually apparent. Eight phenotypes, including arrested and enhanced growth, early senescence, multiple shoots, early and late flowering, reduced fertility and drought tolerance were characterized in half of PEP6 transgenic plants, and two phenotypes (arrested growth and early senescence) were scored in the PEP12 population (see Table 3). Some plants showing multiple growth defects were recorded in each phenotype.

PEP6-3 Transgenic Seedlings Require Sucrose

T1 seeds containing PEP6-3 peptides failed to properly develop if grown on sucrose-free medium. If these seedlings were transplanted to media supplemented with 2% sucrose some of them survived. These surviving seedlings were genotyped. One of these seedlings grew on a sucrose plate for one month and in soil for another 2 months before bolting and setting seeds. The rpORF was re-cloned and transformed into Col-0 Arabidopsis to generate independent transformation lines. In total, 20 independent transgenic lines were obtained, and all of them grew smaller than control lines. The T2 seeds from the original line and 5 independent lines were sown on a ½ MS plate with or without sucrose under kanamycin selection. Seeds on both types of media germinated at a rate of 95%. Kanamycin selection indicated that 90% of germinated T2 seedlings were transgenic lines. All germinated seeds on sucrose plates grew into fully-developed plants. While germination was comparable in the absence of sucrose, the transgenic seedlings grew slowly and presented only yellow cotyledons and first two true leaves, with <30% forming true leaves and <10% growing into fully-developed plants. Only 50% of non-transgenic controls developed true leaves and most of them were able to grow into fully-developed plants, indicating that the seedlings were challenged to mature without a carbon source (FIGS. 10A-10D). The effect of the peptide was tested in petunia. Five independent transgenic shoots were obtained that tested positive for the PEP6-3 transgene (SEQ ID NO: 13), but they grew slowly compared to controls before turning pale and dying after several weeks (FIG. 10D). Thus, the BARP for PEP6-3 (SEQ ID NO: 14, nucleotide sequence SEQ ID NO: 13) appears to produce phenotype that requires sucrose media.

Transgenic Plants with PEP6-15 Exhibit Early Flowering

A number of random-peptide containing plants exhibited an early flowering phenotype, which prompted us to investigate the connection between rpORFs and flowering time. T2 seeds were grown from transgenic plants showing early flowering directly in soil and compared their flowering time with wild type Col-0. The first PEP6-15 transgenic plant was originally characterized as a small and early flowering plant and its T2 seedlings repeated the flowering phenotype but not the plant size. The rpORF were cloned from this seedling PEP6-15 and retransformed into Col-0. A total of 15 indepedent transgenic lines were isolated and measured on their flowering time. About 75% independent lines had earlier flowering time compared to wild type plants. Thereafter three representative lines 1, 2 and 3, were chosen for detailed analyses (FIG. 11A). All three lines had 10 rosette leaves compared to 11.5 rosette leaves in Col-0 when they were bolting (FIG. 11B), which indicated that transgenic lines bolted 3-4 d earlier. Thus, the BARP for PEP6-15 (SEQ ID NO: 6, nucleotide sequence SEQ ID NO: 17) appears to produce an earlier flowering time phenotype.

Transgenic Plants with PEP6-32 Exhibit Impaired Response to Red Light

Seedlings from the PEP6-32 line (nucleotide sequence SEQ ID NO: 24, peptide sequence SEQ ID NO: 10) exhibited slightly longer hypocotyls under red light conditions. The seedlings were then grown in darkness and under narrow-bandwidth conditions. The PEP6-32 seedlings exhibited insensitivity specific to red light. Next, the PEP6-32 construct was reintroduced into independent transgenic lines that were isolated and analyzed on their sensitivities to various fluence rates of different wavelengths of light. The red-light insensitivity defect was observed clearly in eight of the ten independent lines. Four of the lines were examined for photomorphogenic responses. In darkness, seedling growth was comparable to wild-type seedlings. Under constant red light all four peptide-containing lines exhibited longer hypocotyls than wild-type controls, when grown under fluence rates of 1, 10 and 50 $\mu mol \cdot m^{-2} \cdot s^{-1}$ (FIGS. 12A-12B). When examined under other wavelengths the effect was not as pronounced (FIGS. 13A-13B). Seedlings grown under 0.5 $\mu mol \cdot m^{-2} \cdot s^{-1}$ blue light exhibited slightly longer hypocotyls, but differences were not observed at higher fluence rates of 2 and 10 $\mu mol \cdot m^{-2} \cdot s^{-1}$ (FIG. 13A). No significant differences were observed under far red light conditions, including low fluence rate conditions where hypocotyl lengths approximated those where red light effects were evident (FIG. 13B). Thus, the BARP for PEP6-32 (SEQ ID NO: 10, nucleotide sequence SEQ ID NO: 24) appears to produce a red light insensitivity phenotype.

Frequent Aberrant Phenotypes

A number of atypical phenotypes were observed frequently yet do not appear to be sequence dependent. Approximately one percent of seedlings would germinate and die in the agar, and were noted because they were GFP positive. Approximately one to three percent of transgenic seedlings exhibited hyperhydricity (vitrification), noted as fragile, translucent, light green seedlings in culture. The plants did not typically survive when moved to soil and rarely flowered in culture or in soil. Some did transition to true leaves in soil and flowered, and normally-developed seedlings did not exhibit hyperhydricity. The sequences contained in these backgrounds presented no common features in the randomized portion of the sequence, and there was no trend upon translation prediction.

Discussion

The approach demonstrated in this example provides in vivo reverse chemical genomics, or perhaps a combination of synthetic biology and chemical genomics. Chemical genomics is a well-established technique where libraries of known compounds are assessed for unanticipated function. Compounds in these collections incidentally interfere with, or sometimes enhance, biological processes. Phenotypes identified from chemical genomics screens unveil potential roles for new molecules that modulate plant behaviors or traits. Chemical genomics can also inform understanding of receptor and signaling function, with identification of novel chemistries that orthogonally introgress into known biochemical processes by molecular happenstance.

The approach presented in the current work provides additional evidence that random peptides can affect discrete biological processes via specific biochemical interactions. Instead of being applied from a library of compounds as in a chemical genomics screen, novel molecules are produced in the plant itself, with each plant in a population producing a unique cyclical peptide.

With the installation of randomness we circumvent evolution's pull on peptide design and introduce unique molecules into the context of the plant biochemistry. The goal is to identify new potential growth regulators, developmental modulators or even new classes of molecules that could have roles as insecticides, fungicides, nematicides.

The new phenotypes characterized in this work are a just a few of many. Plants featuring early and late flowering tendencies, larger rosette diameters, flowers without stamens, abaxialized leaves, root-length variation, and many other phenotypes have been observed that appear to be discrete lesions in plant biology. These are now being characterized. In the present example, FIGS. 2A-2D show the possibility of identifying new compounds that could act as next-generation herbicides.

As described in the results, above, the seedlings transformed with the sequence encoding PEP6-3 (SEQ ID NO: 14) can only grow if placed on media containing sucrose, suggesting a defect in carbon fixation that may be overcome with growth on a carbon source. PEP6-3 also shows lethal effects in petunia, demonstrating a general effect in plants. PEP6-3 is not likely functioning as known photosynthetic herbicides do, either in diverting chloroplast electron transport (e.g. Moreland, 1980) or interfering with pigment production (e.g. protoporphoinogen inhibitors; Duke et al., 1991), as the plants are completely normal when moved to sucrose. The mechanism of action is being explored.

FIG. 11A shows plants that harbor PEP6-15 (SEQ ID NO: 6) consistently flower early. Flowering is a process coordinated by multiple interacting pathways (the complexity depicted well in Blumel et al., 2015), and genetic analysis may reveal where this peptide is interconnecting with these well-established networks to hasten this developmental transition. Such peptides could have value in controlling the timing of crop production, helping growers to match plant behavior with high-value market windows, weather, or labor availability.

Seedling stem elongation is suppressed by light (Parks et al., 2001). However, the PEP6-32 seedlings (expressing the BARP having SEQ ID NO: 10) exhibit the same hypocotyl length as controls in darkness, yet longer stems under red light (FIGS. 12A-12B). The effect is less pronounced under blue or far-red light (FIG. 13A-13B). The results suggest that the peptide could be interfering on the input side of phytochrome B (phyB) signaling. The phyB photoreceptor responds to red light and is known to control many aspects of plant stature and development, including shade response (Keller et al., 2011) and flowering control (Valverde et al., 2004). The slight effects in blue light are consistent with impaired phyB function (Neff and Chory, 1998). Additional experiments will examine the role of this peptide in discrete red-light mediated processes, as well as test interactions with phyB signaling components.

Other atypical morphologies were noted with a relatively high frequency, between 1-3% of seedlings, with no obvious connection to the amino acid sequence. The plants fit into three categories: dwarf plants, plants exhibiting hyperhydricity (vitrification), and plants that simply died immediately after germination. Dwarf plants were frequent, and could be caused by a suite of mechanisms spanning everything from hormones to defense. There also were a substantial number of seedlings that germinated and were GFP positive, yet never developed beyond emerged cotyledons and a shed seed coat. Many of these were recovered from selective media and transplanted into complete nutrient media for rescue and characterization, yet effects were invariably lethal. These seedlings were not quantified or investigated in this primary study, but the causal sequences could eventually be of significant value to future efforts in identifying plant-lethal peptides.

Another frequent class of seedlings exhibited hyperhydricity, a condition observed by plants regenerated in tissue culture (Kevers et al., 2004). The syndrome is characterized by fragile, pale green leaves that are almost translucent, a condition previously described as vitrification. At the cellular level there are many defects in vitrified plants, including the lack of palissade cells, large vacuoles in spongy mesophyll, few stomata, low/no lignification, and few vascular bundles and hypertrophy in stem parenchyma (Gaspar et al., 1987). Hyperhydricity is a stress-induced state where differentiation is restricted and plants appear to be attaining a state where they can survive in the presence of stress from culture.

It is unclear why these plants were occurring at such a high frequency. It had not escaped our notice that peptides formed from degradation of proteins via the proteasome can function as specific signaling molecules. Ramachandran and Margolis (2017) noted that peptides created by a membrane-associated proteasome in neurons had a role in calcium signaling, and that calcium events could be affected by the peptides themselves when proteasome activity was blocked. It is possible that certain classes of peptides, or perhaps an overabundance of peptides that are stable in the cell, may induce a stress response leading to hyperhydricity. This phenotype is curious and will be investigated more closely, along with its ties to peptide sequence or abundance.

This approach lends itself to development of new chemistries that could potentially work in specific plant taxa, or compounds that could have reduced environmental or health impacts compared to currently available herbicides and growth regulators. One possible issue is that these small, cyclical peptides could be possibly subjected to many physical and chemical constraints that would make them unlikely to be effective if applied to plants directly. Technology exists to facilitate application. The peptides identified here could conceivably be fused to cell-penetrating peptides or leader sequences with a cleavage site that could be processed by resident proteases. Delivery may also be facilitated by nanoparticle-mediated methods, liposomes, or other methods of encapsulation that permit transit into cells.

It is also possible to add sequences to stabilize a peptide within the organism, or add sequences to deliver it to specific intracellular compartments (Ladner et al., 2004). A class of compounds known as "mimetic peptides" may produce a similar chemical signature to the cell without being subject to resident surveillance or turnover mechanisms. Mimetic peptides impart pharmacological effects by binding to receptors, disrupting enzymes or acting as decoys-binding ligands that would have instead activated signal transduction networks (Cardó-Vila et al., 2010). They function because they bear structural similarity to biologically active L-amino acids, but are composed of D-form amino acids. This change in enantiomeric forms produces inverted-derivative peptides that are more likely to evade innate recognition and turnover mechanisms, such as proteases that could limit the half-life or effect of the compound (Adessi and Soto, 2002).

In the larger scope of growth regulator design, their value is not restricted to their peptide nature. The short runs of amino acids produced here can simply be thought of as a rogue, engineered chemistry that integrates with biology in an unintended way to impart a biological effect. That information alone exposes plant vulnerabilities or opportunities for growth regulator development. These findings may serve as the basis for sophisticated chemical modeling and production of novel compounds with new biological targets, extending beyond plants to bacteria, fungi and even animals.

The present example demonstrates that multiple, reproducible phenotypical outcomes can be induced in planta with the installation of random DNA sequence that encodes cyclized peptides. The original templates for the PEP6 and PEP12 libraries have 18 and 36 random nucleotides theoretically representing between 69 billion and $4^{36}$ possible DNA sequence combinations, respectively. In these trials over 2,000 independent plant transformations were examined, and the present example demonstrates at least three intriguing reproducible candidates that present clear opportunities for further development for potential commercial application. Many other phenotypes were observed and the causal sequences are being characterized. The high frequency of phenotype discovery underscores the power of this method.

It is also a possibility that the effects seen arise from the RNA being generated and not the peptide itself. The highly-expressed random sequences could find homology with RNA, triggering a silencing response. While not generating random peptides, these sequences are still valuable, and may be examined further by performing a basic BLAST search against the *Arabidopsis* expressed sequences. Alternatively, sequences may be installed where the third codon base is changed in the transgenic sequence, producing the same peptide with a different RNA sequence. Even if the effect is additive, applications are possible, as interfering RNA is now being applied to plants to induce desired control of gene expression in the plant and pathogens (Mitter et al., 2017).

This Example provided evidence that overexpression of cyclical small random peptides provides a screening method that can unveil new candidates for chemistries that modify plant biology. These trails have produced dozens of new candidates that interfere with discrete plant processes.

Materials and Methods

Generation of Random-Core Peptide Libraries

DNA oligonucleotides encoding peptides $MACX_6C$ (PEP6, six random amino acid peptides) or $MGCX_{12}C$ (PEP12, twelve random amino acid peptides) flanked with partial attB1 and attB2 sequences were used as templates for PCR-based amplification. As illustrated in FIG. 9, both PEP6 (SEQ ID NO: 11) and PEP12 (SEQ ID NO: 12) DNA oligonucleotides contain part of attB1 and attB2 sequences, two nucleotides "CC" in front of "ATG" for in-frame expression and ending sequence "TGTTAG" (nt. 42-47 of SEQ ID NO: 11, and nt. 60-65 of SEQ ID NO: 12). PEP6 initiates with the sequence "ATGGCCTGT" (nt. 15-23 of SEQ ID NO: 11) followed by 18 random nucleotides, and PEP12 initiates with the sequence "ATGGGCTGT" (nt. 15-23 of SEQ ID NO: 12) followed by 36 random nucleotides. Both DNA oligoes are amplified with attB1 and attB2 primers, and recombined into the entry vector pDONR222 through BP reactions to generate two entry libraries. Entry libraries are recombined into the destination vector pK7WD2D vector through LR reactions to create two destination libraries.

The library inserts were amplified using attB universal adaptor primers (SEQ ID NOs: 33 and 34) listed in Table 4 (FIG. 9). PCR products were cloned into the entry vector pDONR222 with the BP reaction following the manufacture's procedure (Cat. #11789020, Invitrogen ThermoFisher Scientific). Plasmids were extracted from bulked bacterial transformants and referred as PEP6 and PEP12 entry libraries. The entry libraries were recombined with the destination binary vector pK7WG2D (Karimi et al., 2002, hereby incorporated by reference herein) to create PEP6 and PEP12 destination libraries through LR reactions following the manufacture's procedure (Cat. #11791020, Invitrogen ThermoFisher Scientific) and transformed into *E. coli*. Approximately 9000 transformed bacterial colonies were harvested from four 245 mm by 245 mm square plates (Cat. #240835 ThermoFisher Scientific) to prepare PEP6 destination library bulked plasmid DNA. Bulked plasmids were transformed into *Agrobacterium tumefaciens* GV3101 for plant transformation with each of the destination libraries.

Transformation and Isolation of Transgenic *Arabidopsis* Plants

Bolting plants with multiple inflorescences were transformed with the PEP6 or PEP12 destination library through the floral dipping method (Clough and Bent, 1998, incorporated herein by reference). For selection, seeds were surface sterilized by 70% ethanol for 5 min and 10% bleach for 20 min. Surface-sterilized seeds were plated on ½× MS basal medium with 0.5% Phyto Agar (cat. # M10200 and # A20300, Research Products International) and 50 µg/ml kanamycin for selection. Transgenic seedlings were identified by GFP expression or resistance to kanamycin. Transformed seedlings were grown to the 3-5 true leaf stage on plates and transferred to soil. DNA was extracted from each seedling (Edwards et al., 1991 incorporated herein by reference) for inserted nucleotide sequence identification. An approximately 500 bp DNA fragment containing the random peptide ORF and part of pK7WG2D vector sequence was amplified using primers PEP-F and PEP-R (SEQ ID NOs: 35 and 36, respectively) listed in Table 4 and sequenced.

Plant Growth and Phenotyping

*Arabidopsis* plants were grown in soil at 20° C. under 16 hour light/8 hour dark conditions. The characterization of phenotypic variations was based on the comparison among seedlings grown in the same pot or flat. Plants exhibiting phenotypes were tagged and monitored for atypical growth throughout their development.

Confirmation in Independent Transformation Events

It is possible that the phenotypes observed were not related to the peptide sequence, but instead were artifacts of T-DNA integration, since insertion of the CaMV35S-bearing T-DNA cassette could potentially disrupt a gene where an effect could be observed in its heterozygous form, or the viral promoter could activate expression of neighboring genes, resulting in an observable phenotype. Thus, to generate a series of independent transformants for each sequence of interest, the random peptide ORFs from transgenic plants showing aberrant phenotypes were amplified using attB universal adaptor primers, and cloned into pDONR222 and pK7WG2D vectors via BP and LR reactions, respectively. These constructs were then transformed into *Arabidopsis* to generate additional independent transgenic lines. Each series of independent transgenic lines containing the same random peptide ORF were grown under the same conditions used to produce the original phenotype. Transcript abundance of the random peptide ORF and the control gene Ubiquitin family protein (UFP, At4g01000) in every transgenic line was analyzed by semi-quantitative RT-PCR using attB1 and attB2 adaptor primers or UFP-rF and -rR primers (SEQ ID NOs: 37-38), respectively. All primer sequences are listed in Table 4.

Petunia Transformation

PEPS-3 was introduced into *Petunia* hybrida by *Agrobacterium tumefaciens*-mediated transformation of leaf fragments, following a modified protocol by Jorgensen et al, (1996), incorporated herein by reference. Leaves were dissected into 4×5 mm fragments and immersed in *Agrobacterium* solution for 15 min, then transferred to MS agar plates supplemented with TDZ (1 µg/mL), galacturonic add (212 µg/mL) and acetosyringone (8 µg/mL). After 2 d in darkness, explants were transferred to MS medium containing TDZ (1 µg/mL), carbenicillin (500 µg/mL) and kanamycin (150 µg/mL) for two weeks. Callusing explants were then transferred to light on MS medium containing only antibiotics. After the appearance of shoots, these were transferred to MS medium containing antibiotics and IBA (0.8 µg/mL), for root formation.

Effects of Lethal Sequences

The T1 seedling with PEP6-3 peptide sequence (SEQ ID NO: 14) exhibited a severe arrested-development phenotype at the early seedling stage, yet was GFP positive. The seedling was moved to media containing sucrose where it then developed normally. Five independent lines (1, 2, 3, 4 and 6) containing the PEP6-3 sequence (SEQ ID NO: 13) were grown under kanamycin selection on ½ MS medium with or without the supplement of 2% sucrose in dark for the first 7 d and then exposed to light. Without sucrose, some seedlings with only the two cotyledons or the first two true leaves died eventually, and only a few seedlings fully developed. The proportion of seedlings developed with the first two true leaves or fully developed was recorded.

plates were transferred to various light conditions of varying spectral quality and fluence rates (as described in FIGS. 12A-12B), or complete darkness. The light sources used were LED based and emitted at 470 nm (blue), 660 nm (red) and 730 nm (far-red). Plants grown in darkness were placed under one of the narrow bandwidth treatments wrapped in two layers of aluminum foil. After 96 h the plates were scanned and the seedlings were measured using ImageJ software, and the length of the seedlings was reported as a fraction of dark-grown seedling length.

Statistical Analyses

Data were analyzed in excel or R (htttps://www.r-project.org/). The statistical analyses were performed in R using Mann-Whitney U test or Student's t-test for normally-distributed data.

Tables:

TABLE 2

(SEQ ID NOs: 6, 10, and 13-32)

| Plant ID | rosette size (mm) | Nucleotide Sequence | SEQ ID NO | Peptide sequence | SEQ ID NO |
|---|---|---|---|---|---|
| PEP6-1 | 30 | NA | NA | NA | NA |
| PEP6-2 | 26 | NA | NA | NA | NA |
| PEP6-3 | 5 | atggcctgtcgtggtgttgatagtgcttgttag | 13 | MACRGVDSAC | 14 |
| PEP6-12 | 5 | atggcctgttggatgtcgaggatggagtgttag | 15 | MACWMSRMEC | 16 |
| PEP6-15 | 5 | atggcctgtgatttaattttggtatttgttag | 17 | MACDFNFGIC | 6 |
| PEP6-27 | 8 | atggcctgtaattgttcttctgatggttgttag | 18 | MACNCSSDGC | 19 |
| PEP6-28 | 8 | atggcctgtcagctgatgtggcgggagtgttag | 20 | MACQLMWREC | 21 |
| PEP6-30 | 10 | atggcctgtcaggagctgacgatgtggtgttag | 22 | MACQELTMWC | 23 |
| PEP6-32 | 27 | atggcctgtcctgcttctgttagtgtttgttag | 24 | MACPASVSVC | 10 |
| PEP6-33 | 9 | atggcctgtcctaatgcttgtttttcttgttag | 25 | MACPNACFSC | 26 |
| PEP6-37 | 8 | atggcctgtcagcagatgttgtcggggtgttag | 27 | MACQQMLSGC | 28 |
| PEP6-38 | 8 | atggcctgttctgatgttagtgttatttgttag | 29 | MACSDVSVIC | 30 |
| PEPB-46 | 10 | atggcctgtggtggtggttgttctgcttgttag | 31 | MACGGGCSAC | 32 |

Flowering Time Measurement

Transgenic plants with the PEP6-15 gene (SEQ ID NO: 17) exhibited earlier bolting time compared to controls (other genotypes with the same cassette but different peptide sequence). Three independent PEP6-15 transgenic lines with no transgene segregation were grown directly in soil for the measurement of flowering time. Every line was planted in three 10 cm×10 cm×11 cm pots, and approximately twenty seeds were sown in each pot. The flowering time was recorded as the number of rosette leaves when the inflorescence stem was 0.5-1 cm long. When the majority of plants had flowered, measurement was concluded.

Inhibition of Hypocotyl Elongation

Seedlings from the PEP6-32 line (SEQ ID NO: 24, peptide seq SEQ ID NO: 10) possessed slightly longer hypocotyls than other seedlings grown under white light, so this line was examined more closely under different spectral conditions. Seeds were surface sterilized using a brief treatment of 70% ethanol and then set to dry on sterile paper discs in a laminar flow hood. The seeds were placed on 1 mM KCl plus 1 mM CaCl$_2$ media containing 1% Phyto Agar on 100 mm square plates and stratified for 48 h. The vertical

TABLE 3

| Small ORFs | PEP6 | PEP12 |
|---|---|---|
| Total | 752 | 637 |
| Survival rate | −1.8% | −1.2% |
| Phenotypes | | |
| Arrested growth | 50 | 53 |
| Enhanced growth | 4 | NA |
| early senescence | 36 | >2 |
| Multiple shoots | 371 | NA |
| Drought tolerant | 17 | NA |
| early flowering | 114 | NA |
| late flowering | 184 | NA |
| Reduced fertility | 41 | NA |
| Retransformed | 47 | 5 |

TABLE 4

(SEQ ID NOs: 33-38)

| Primer Name | Sequence | SEQ ID NO |
|---|---|---|
| att81 adaptor primer: | GGGGACAAGTTTGTACAAAAAAGCAGGCT | 33 |
| att82 adaptor primer: | GGGGACCACTTTGTACAAGAAAGCTGGGT | 34 |
| PEP-F: | CGTAAGGGATGACGCACAATCC | 35 |
| PEP-R: | GAGCGAAACCCTATAAGAACCC | 36 |
| UFP-rF: | CCAGCAGACATGGAGGTTTTGGGG | 37 |
| UFP-rR: | TGTTGTCTGTCATTTCTTGGCCAGT | 38 |

Example 3 References

Adessi C, Soto C (2002) Converting a peptide into a drug: strategies to improve stability and bioavailability. Current medicinal chemistry 9: 963-978

Blümel M, Daily N, Jung C (2015) Flowering time regulation in crops—what did we learn from *Arabidopsis*? Current Opinion in Biotechnology 32: 121-129

Breiden M, Simon R (2016) Q&A: How does peptide signaling direct plant development? BMC Biology 14: 58

Cardó-Vila M, Giordano R J, Sidman R L, Bronk L F, Fan Z, Mendelsohn J, Arap W, Pasqualini R (2010) From combinatorial peptide selection to drug prototype (II): Targeting the epidermal growth factor receptor pathway. Proceedings of the National Academy of Sciences 107: 5118-5123

Clough S J, Bent A F (1998) Floral dip: a simplified method for Agrobacterium-mediated transformation of *Arabidopsis thaliana*. Plant J 16: 735-743

Duke S O, Lydon J, Jos, xe, Becerril M, Sherman T D, Lehnen L P, Matsumoto H (1991) Protoporphyrinogen Oxidase-Inhibiting Herbicides. Weed Science 39: 465-473

Edwards K, Johnstone C, Thompson C (1991) A simple and rapid method for the preparation of plant genomic DNA for PCR analysis. Nucleic Acids Res 19: 1349

Gaspar T, Kevers C, Debergh P, Maene L, Paques M, Boxus P (1987) Vitrification: Morphological, Physiological, and Ecological Aspects. In J M Bonga, D J Durzan, eds, Cell and Tissue Culture in Forestry: General Principles and Biotechnology. Springer Netherlands, Dordrecht, pp 152-166

Hamzeh-Mivehroud M, Alizadeh A A, Morris M B, Bret Church W, Dastmalchi S (2013) Phage display as a technology delivering on the promise of peptide drug discovery. Drug Discovery Today 18: 1144-1157

Higashijima T, Uzu S, Nakajima T, Ross E M (1988) Mastoparan, a peptide toxin from wasp venom, mimics receptors by activating GTP-binding regulatory proteins (G proteins). Journal of Biological Chemistry 263: 6491-6494

Jorgensen R A, Cluster P D, English J, Que Q, Napoli C A (1996) Chalcone synthase cosuppression phenotypes in petunia flowers: comparison of sense vs. antisense constructs and single-copy vs. complex T-DNA sequences. Plant molecular biology 31: 957-973

Karimi M, Inze D, Depicker A (2002) GATEWAY vectors for *Agrobacterium*-mediated plant transformation. Trends Plant Sci 7: 193-195

Keller M M, Jaillais Y, Pedmale U V, Moreno J E, Chory J, BaHare C L (2011) Cryptochrome 1 and phytochrome B control shade-avoidance responses in *Arabidopsis* via partially independent hormonal cascades. The Plant Journal 67: 195-207

Kevers C, Franck T, Strasser R J, Dommes J, Gaspar T (2004) Hyperhydricity of Micropropagated Shoots: A Typically Stress-induced Change of Physiological State. Plant Cell, Tissue and Organ Culture 77: 181-191

Ladner R C, Sato A K, Gorzelany J, de Souza M (2004) Phage display-derived peptides as therapeutic alternatives to antibodies. Drug Discovery Today 9: 525-529

Lindell T J, Weinberg F, Morris P W, Roeder R G, Rutter W J (1970) Specific inhibition of nuclear RNA polymerase II by alpha-amanitin. Science 170: 447-449

Mitter N, Worrall E A, Robinson K E, Li P, Jain R G, Taochy C, Fletcher S J, Carroll B J, Lu G Q M, Xu Z P (2017) Clay nanosheets for topical delivery of RNAi for sustained protection against plant viruses. Nature Plants 3: 16207

Moreland D E (1980) Mechanisms of action of herbicides. Annual Review of plant physiology 31: 597-638

Neff M M, Chory J (1998) Genetic interactions between phytochrome A, phytochrome B, and cryptochrome 1 during *Arabidopsis* development. Plant Physiol 118: 27-35

Nixon A E, Sexton D J, Ladner R C (2014) Drugs derived from phage display: From candidate identification to clinical practice. mAbs 6: 73-85

Parks B M, Folta K M, Spalding E P (2001) Photocontrol of stem growth. Curr Opin Plant Biol 4: 436-440

Ramachandran K V, Margolis S S (2017) A mammalian nervous-system-specific plasma membrane proteasome complex that modulates neuronal function. Nat Struct Mol Biol 24: 419-430

Smith G P, Petrenko V A (1997) Phage Display. Chemical Reviews 97: 391-410

Valverde F, Mouradov A, Soppe W, Ravenscroft D, Samach A, Coupland G (2004) Photoreceptor regulation of CONSTANS protein in photoperiodic flowering. Science 303: 1003-1006

Sequences:

SEQ ID NO: 1 (nucleotide sequence of a test nucleic acid encoding a random peptide sequence (candidate BARP), where "n" is any nucleotide. Double underlining indicates Gateway flanking region, single underlining indicates start/stop codons, and bold indicates cysteine codons)

aaaaggaggctccatggcctgtnnnnnnnnnnnnnnnnnnnntgttagaccc

SEQ ID NO: 2 (peptide sequence of BARP associated with purple pigment accumulation in seed pod, "RS$_1$ plant")

MACGKGSGLC

SEC ID NO: 3 (peptide sequence of BARP associated with "bushy seedling")

MACDFLADLC

SEQ ID NO: 4 (peptide sequence of BARP associated with strange seedling characteristics, "EA$_2$ plant")

MACSAHCSDC

SEQ ID NO: 5 (portion of SEQ ID NO: 1 (nt 14-47) corresponding to an embodiment of a candidate BARP without the flanking Gateway® sequences, including start/stop codons, Ala spacer codon, flanking cysteines, and the random sequence of 18 nucleotides ("n") representing codons for six random amino acids)

atggcctgtnnnnnnnnnnnnnnnnnntgttag

SEQ ID NO: 6 (peptide sequence of BARP CBF6AA-15 associated with early flowering)

MACDFNFGIC

SEQ ID NO: 7 (peptide sequence of BARP CBF6AA-85 associated with large, flat leaves with small petioles and having a stop codon, represented below as "X")

MACKQAXQRC

SEQ ID NO: 8 (peptide sequence of BARP CBF6AA-110 also associated with large, flat leaves with small petioles)

MACWTSSVLC

SEQ ID NO: 9 (peptide sequence of BARP 12AA-97 associated with arrested plant growth)

MGCVCIEPYQRLRAKC

SEQ ID NO: 10 (peptide sequence of BARP 6AA-33.1 associated with salt resistance and root growth)

MACPASVSVC

SEQ ID NO: 11
(nucleotide sequence of a test nucleic acid encoding a random peptide sequence having 6 random amino acids (candidate BARP), where "n" is any nucleotide. Double underlining indicates Gateway flanking region, single underlining indicates start/stop codons, and bold indicates cysteine codons. (Nucleotides 2-51 of SEQ ID NO: 11 correspond to SEQ ID NO: 1)

aaaaaggaggctccatggcctgtnnnnnnnnnnnnnnnnnntgttagacccagctttct

SEQ ID NO: 12
(nucleotide sequence of a test nucleic acid encoding a random peptide sequence having 12 random amino acids (candidate BARP), where "n" is any nucleotide. Double underlining indicates Gateway flanking region, single underlining indicates start/stop codons, and bold indicates cysteine codons. (same as SEQ ID NO: 11, except nt. 19 is g instead of c, and it has 18 additional "n" nucleotides)

aaaaaggaggctcc
atgggcctgtnnnnnnnnnnnnnnnnnnnnnnnnnn
nnnnnnnntgttagacccagctttct SEQ ID NOs: 13-32 appear in Table 2 above
SEQ ID NO: 13 (nt sequence encoding BARP PEP6-3)
SEQ ID NO: 14 (peptide sequence of BARP PEP6-3)
SEQ ID NO: 15 (nt sequence encoding BARP PEP6-12)
SEQ ID NO: 16 (peptide sequence of BARP PEP6-12)
SEQ ID NO: 17 (nt sequence encoding BARP PEP6-15, the peptide sequence of which corresponds to SEQ ID NO: 6 from Example 2)
SEQ ID NO: 18 (nt sequence encoding BARP PEP6-27)
SEQ ID NO: 19 (peptide sequence of BARP PEP6-27)
SEQ ID NO: 20 (nt sequence encoding BARP PEP6-28)
SEQ ID NO: 21 (peptide sequence of BARP PEP6-28)
SEQ ID NO: 22 (nt sequence encoding BARP PEP6-30)
SEQ ID NO: 23 (peptide sequence of BARP PEP6-30)
SEQ ID NO: 24 (nt sequence encoding BARP PEP6-32, the peptide sequence of which corresponds to SEQ ID NO: 10 from Example 2)
SEQ ID NO: 25 (nt sequence encoding BARP PEP6-33)
SEQ ID NO: 26 (peptide sequence of BARP PEP6-33)
SEQ ID NO: 27 (nt sequence encoding BARP PEP6-37)
SEQ ID NO: 28 (peptide sequence of BARP PEP6-37)
SEQ ID NO: 29 (nt sequence encoding BARP PEP6-38)
SEQ ID NO: 30 (peptide sequence of BARP PEP6-38)
SEQ ID NO: 31 (nt sequence encoding BARP PEP6-46)
SEQ ID NO: 32 (peptide sequence of BARP PEP6-46)
SEQ ID NOs: 33-38 appear in Table 4 above
SEQ ID NO: 33 (primer attB1 adaptor primer)
SEQ ID NO: 34 (primer attB2 adaptor primer)
SEQ ID NO: 35 (primer PEP-F)
SEQ ID NO: 36 (primer PEP-R)
SEQ ID NO: 37 (primer PEP-rF)
SEQ ID NO: 38 (primer PEP-rR)

The invention claimed is:

1. A method for identifying biologically active random peptides (BARPs) in plants, the method comprising:
providing a library of test nucleic acid sequences, the library comprising a plurality of different test nucleic acid sequences encoding a plurality of candidate BARPs, wherein each test nucleic acid sequence consists of nucleic acids encoding, in the following order: a start codon, a spacer codon selected from alanine or glycine, a first cystine residue, a random sequence of 6-20 amino acids representing a candidate BARP, a second cysteine residue, such that the first and second cysteine residues flank the random sequence of amino acids, and a stop codon, and wherein each test nucleic acid sequence in the library is flanked by recombinatorial cloning primer sequences;
creating a library of recombination vectors from the library of test nucleic acid sequences, wherein each vector comprises a test nucleic acid sequence from the library and a nucleic acid sequence encoding a selectable marker operably linked to the test nucleic acid sequence;
transforming a plurality of phenotypically homogenous Arabidopsis thaliana plants with the library of recombination vectors, wherein the test nucleic acid sequence integrates randomly into each plant genome;
screening the Arabidopsis thaliana plants for the presence of the selectable marker and selecting plants with the selectable marker, wherein identification of the selectable marker indicates expression of a candidate BARP by the plant;
collecting seeds from transformed Arabidopsis thaliana plants, screening seeds or seedlings for the presence of the selectable marker, and growing Arabidopsis thaliana plants from the seeds or seedlings to produce a library of transformed Arabidopsis thaliana plants, wherein each plant comprises a recombination vector from the library;
screening the library of transformed Arabidopsis thaliana plants throughout development for the occurrence of a plant with a new phenotype, wherein the new phenotype is discernible from the phenotype of a corresponding wild type Arabidopsis thaliana plant without the candidate BARP and wherein the presence the new phenotype indicates the candidate BARP in the plant with the new phenotype is responsible for the new phenotype; and
determining the sequence of the candidate BARP from the plant with the new phenotype.

2. The method of claim 1, further comprising, verifying the new phenotype associated with the candidate BARP by independently transforming additional Arabidopsis thaliana plants with a vector encoding the candidate BARP, and screening for the presence of the new phenotype, wherein the presence of the new phenotype in the new transformed plant indicates that the candidate BARP is responsible for the new phenotype.

3. The method of claim 1, wherein the random sequence of amino acids is 6 amino acids in length and each test nucleic acid in the library consists of SEQ ID NO: 5, wherein "n" represents any nucleotide, and wherein each "n" for each test nucleic acid sequence in the library is independently selected.

4. The method of claim 1, wherein the recombination vector encodes two or more different selectable markers, wherein the nucleic acid sequence encoding each selectable marker is operably linked to the test nucleic acid sequence.

5. The method of claim 1, wherein recombination cloning methods are used to generate the library of recombination vectors.

6. The method of claim 5, further comprising transforming a plurality of bacterial cells with the library of recombination vectors and using the transformed bacterial cells to transform the plants.

7. The method of claim 6, wherein the bacterial cells are *Agrobacterium tumefaciens* cells.

8. The method of claim 1, wherein the new phenotype manifests as a general defect, a discrete defect, or both.

9. The method of claim 8, wherein the new phenotype is selected from the group consisting of: early plant death, glassy seedlings, dwarf seedlings, slowed growth, inability to flower, inability to seed, early flowering, differential leaf characteristics, differential pigmentation, arrested development, long roots, bushy growth patterns, light-insensitivity, and differential light-sensitivity.

10. The method of claim 2, further comprising, testing the activity of the candidate BARP in a second plant species by independently transforming plants of a second species other-than *Arabidopsis thaliana* with a vector encoding the candidate BARP, and screening for the presence of the new phenotype, wherein the presence of the new phenotype in the transformed plants of the second plant species indicates that the candidate BARP is responsible for the new phenotype and that the candidate BARP is active in a second plant species.

11. The method of claim 1, wherein each test nucleic acid in the library plus the flanking recombinatorial cloning primer sequences consists of SEQ ID NO: 1, wherein "n" represents any nucleotide, and wherein each "n" for each test nucleic acid sequence in the library is independently selected.

12. The method of claim 1, wherein each test nucleic acid in the library plus the flanking recombinatorial cloning primer sequences consists of SEQ ID NO: 12, wherein "n" represents any nucleotide, and wherein each "n" for each test nucleic acid sequence in the library is independently selected.

* * * * *